United States Patent
Kuhara et al.

(10) Patent No.: US 10,338,177 B2
(45) Date of Patent: Jul. 2, 2019

(54) MAGNETIC RESONANCE IMAGING APPARATUS, MAGNETIC RESONANCE IMAGING METHOD AND MAGNETIC RESONANCE IMAGING SYSTEM

(71) Applicant: TOSHIBA MEDICAL SYSTEMS CORPORATION, Otawara-shi, Tochigi (JP)

(72) Inventors: Shigehide Kuhara, Tochigi (JP); Shuhei Nitta, Tokyo (JP); Taichiro Shiodera, Tokyo (JP); Tomoyuki Takeguchi, Tokyo (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 1136 days.

(21) Appl. No.: 14/466,330

(22) Filed: Aug. 22, 2014

(65) Prior Publication Data

US 2016/0054417 A1  Feb. 25, 2016
US 2016/0334486 A9  Nov. 17, 2016

Related U.S. Application Data

(63) Continuation of application No. PCT/JP2013/081566, filed on Nov. 22, 2013.

(30) Foreign Application Priority Data

Nov. 22, 2012  (JP) .................................. 2012-256683

(51) Int. Cl.
*G01V 3/00* (2006.01)
*G01R 33/56* (2006.01)
(Continued)

(52) U.S. Cl.
CPC .......... *G01R 33/5608* (2013.01); *A61B 5/055* (2013.01); *G01R 33/4818* (2013.01);
(Continued)

(58) Field of Classification Search
CPC ..................................................... G01R 33/543
(Continued)

(56) References Cited

U.S. PATENT DOCUMENTS 7,148,688 B2    12/2006  Kojima
8,831,703 B2 *   9/2014  van der Kouwe ..... A61B 5/055
                                                 324/307

(Continued)

FOREIGN PATENT DOCUMENTS

JP   2005-296627       10/2005
JP   2006-320527 A     11/2006
(Continued)

OTHER PUBLICATIONS

International Search Report for PCT/JP2013/081566 dated Feb. 18, 2014.

(Continued)

*Primary Examiner* — Louis M Arana
(74) *Attorney, Agent, or Firm* — Nixon & Vanderhye P.C.

(57) ABSTRACT

A magnetic resonance imaging apparatus according to an embodiment includes a sequence control unit, an image generating unit, and a deriving unit. The sequence control unit executes first imaging scan for acquiring data of a range including a target internal organ and second imaging scan for acquiring data for a diagnostic image by controlling execution of a pulse sequence. The image generating unit generates an image by using data acquired by the first imaging scan. The deriving unit derives an imaging scan area in which data for the diagnostic image are acquired in the second imaging scan and a related area set associated (Continued)

with the imaging scan area in the second imaging scan, based on image processing using the image.

22 Claims, 15 Drawing Sheets

(51) Int. Cl.
    *A61B 5/055* (2006.01)
    *G01R 33/54* (2006.01)
    *G01R 33/565* (2006.01)
    *G01R 33/48* (2006.01)
    *G01R 33/483* (2006.01)

(52) U.S. Cl.
    CPC ..... *G01R 33/543* (2013.01); *G01R 33/56509* (2013.01); *G01R 33/4833* (2013.01); *G01R 33/546* (2013.01); *G01R 33/5602* (2013.01)

(58) Field of Classification Search
    USPC ................................. 324/309, 307, 306, 314
    See application file for complete search history.

(56) References Cited

U.S. PATENT DOCUMENTS

| 9,157,979 | B2* | 10/2015 | Miyazaki | G01R 33/5673 |
| 9,636,039 | B2* | 5/2017 | Benner | A61B 5/055 |
| 2009/0005670 | A1 | 1/2009 | Ichinose et al. | |
| 2011/0178388 | A1 | 7/2011 | Kuhara et al. | |
| 2011/0206260 | A1 | 8/2011 | Bergmans et al. | |
| 2011/0234226 | A1 | 9/2011 | Nitta et al. | |
| 2012/0108946 | A1 | 5/2012 | Kuhara | |
| 2013/0154646 | A1 | 6/2013 | Nitta et al. | |
| 2015/0153434 | A1* | 6/2015 | Ooshima | G01R 33/5676 324/309 |

FOREIGN PATENT DOCUMENTS

| JP | 2009-028525 | 2/2009 |
| JP | 2009-106480 | 5/2009 |
| JP | 2011-147561 | 8/2011 |
| JP | 2012-61074 | 3/2012 |
| JP | 2012-507331 | 3/2012 |

OTHER PUBLICATIONS

Japanese Office Action dated Dec. 26, 2017 in JP 2013-242371.
Japanese Office Action in Application No. 2018-058381 dated Jan. 29, 2019 (3 pages).

* cited by examiner

CORONAL IMAGE                AXIAL IMAGE

MAGNETIC RESONANCE IMAGING APPARATUS, MAGNETIC RESONANCE IMAGING METHOD AND MAGNETIC RESONANCE IMAGING SYSTEM

CROSS-REFERENCE TO RELATED APPLICATIONS

This application is a continuation of PCT international application Ser. No. PCT/JP2013/081566 filed on Nov. 22, 2013 which designates the United States, incorporated herein by reference, and which claims the benefit of priority from Japanese Patent Application No. 2012-256683, filed on Nov. 22, 2012, the entire contents of which are incorporated herein by reference.

FIELD

Embodiments described herein relate generally to a magnetic resonance imaging apparatus and a magnetic resonance imaging method.

BACKGROUND

Magnetic resonance imaging is an imaging scan method that magnetically excites nuclear spins of a subject placed in a magnetostatic field by an RF (radio frequency) pulse having a Larmor frequency thereof, to generate an image from magnetic resonance signal data generated with the excitation.

In the magnetic resonance imaging, imaging scan may be performed by setting a related area associated with an imaging scan area in which data for a diagnostic image is acquired, other than the imaging scan area. For example, in an imaging scan method (WH (Whole Heart) MRCA (Magnetic Resonance Coronary Angiography)) in which coronary artery running in the whole heart is imaged, an application area of a motion detection pulse (Motion Probe) for detecting a respiratory motion is set in addition to an imaging scan area including the heart. Furthermore, for example, in a Time-SLIP (Spatial Labeling Inversion Pulse), which is one of the imaging scan methods that selectively draws a blood vessel by ASL (Arterial Spin Labeling), an application area of a tag pulse for labeling blood is set in addition to the imaging scan area.

In this way, in various types of imaging scan, setting of the related area associated with the imaging scan area may be required in addition to the imaging scan area. However, the procedure thereof is complicated and a long time may be often required.

DETAILED DESCRIPTION

A magnetic resonance imaging apparatus according to an embodiment includes a sequence control unit, an image generating unit, and a deriving unit. The sequence control unit executes first imaging scan for acquiring data of a range including a target internal organ and second imaging scan for acquiring data for a diagnostic image by controlling execution of a pulse sequence. The image generating unit generates an image by using data acquired by the first imaging scan. The deriving unit derives an imaging scan area in which data for the diagnostic image are acquired in the second imaging scan and a related area set associated with the imaging scan area in the second imaging scan, based on image processing using the image.

Embodiments of a magnetic resonance imaging apparatus (hereinafter, "MRI (Magnetic Resonance Imaging) apparatus" where appropriate) and a magnetic resonance imaging method will be explained with reference to the accompanying drawings. The embodiments are not limited to the following ones. In addition, in principle, contents explained in each of the embodiments can be similarly applicable to other embodiments.

First Embodiment

Figure 1:
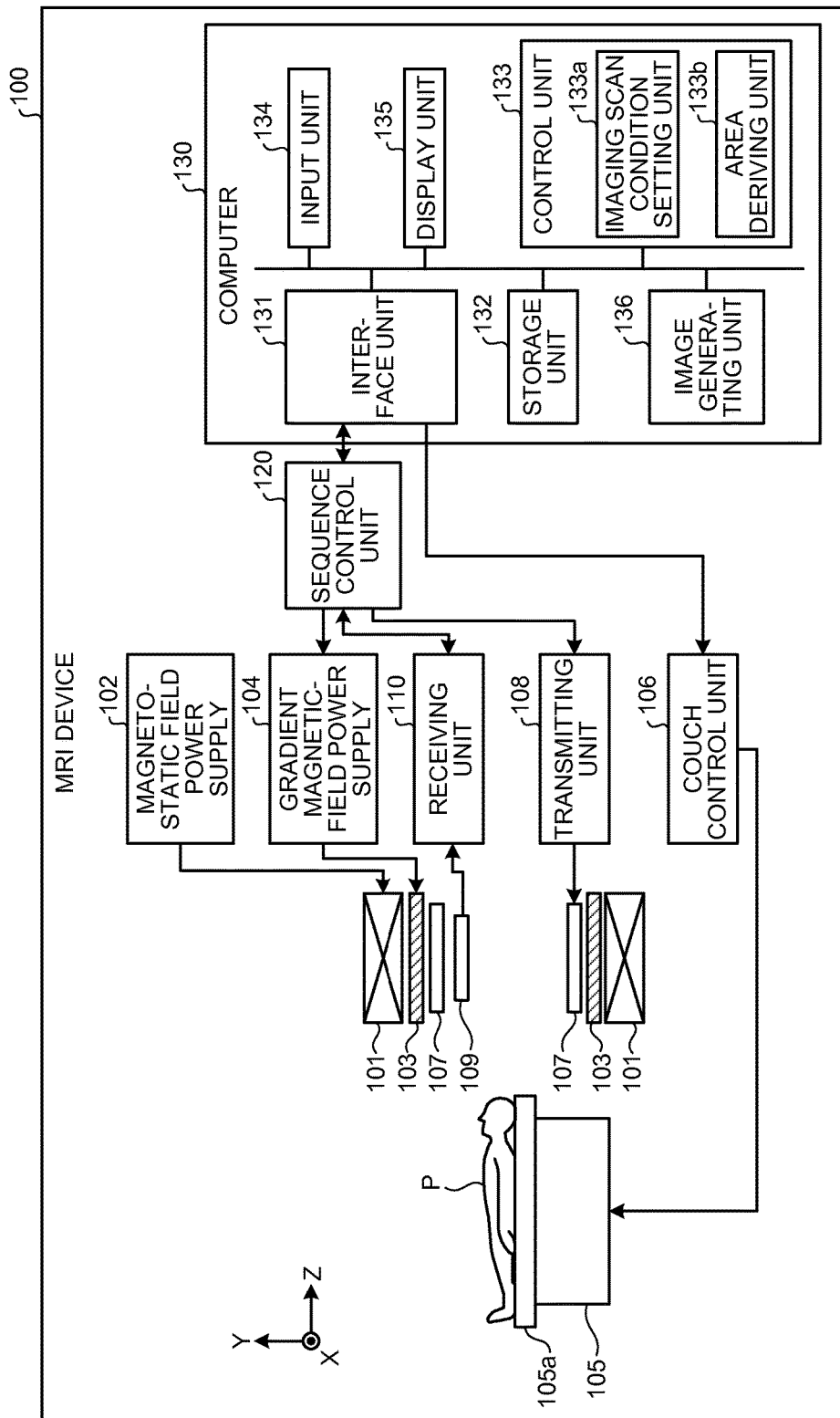
FIG. 1 is a functional block diagram showing a configuration of an MRI apparatus according to a first embodiment.

FIG. 1 is a functional block diagram showing a configuration of an MRI apparatus 100 according to a first embodiment. As shown in FIG. 1, the MRI apparatus 100 includes a magnetostatic field magnet 101, a magnetostatic field power supply 102, a gradient magnetic-field coil 103, a gradient magnetic-field power supply 104, a couch 105, a couch control unit 106, a transmission coil 107, a transmitting unit 108, a reception coil array 109, a receiving unit 110, a sequence control unit 120, and a computer 130. A subject P (for example, a human body) is not included in the MRI apparatus 100. The configuration shown in FIG. 1 is only an example. For example, respective units in the sequence control unit 120 and the computer 130 can be configured to be integrated or separated where appropriate.

The magnetostatic field magnet 101 is a magnet formed in a hollow cylindrical shape and generates a magnetostatic field in an internal space thereof. The magnetostatic field magnet 101 is a superconducting magnet or the like, and is excited upon reception of current supply from the magnetostatic field power supply 102. The magnetostatic field power supply 102 supplies a current to the magnetostatic field magnet 101. The magnetostatic field magnet 101 can be a permanent magnet. In this case, the MRI apparatus 100 may not have to include the magnetostatic field power supply 102. Alternatively, the magnetostatic field power supply 102 can be provided separately from the MRI apparatus 100.

The gradient magnetic-field coil 103 is formed in a hollow cylindrical shape and is arranged inside the magnetostatic field magnet 101. Three coils corresponding to respective X, Y, and Z axes orthogonal to each other are combined to form the gradient magnetic-field coil 103, and these three coils generate a gradient magnetic field in which the magnetic field intensity changes along each of the X, Y, and Z axes upon reception of current supply individually from the gradient magnetic-field power supply 104. The gradient magnetic fields along the respective X, Y, and Z axes generated by the gradient magnetic-field coil 103 respectively correspond to, for example, a gradient magnetic field Gs for slicing, a gradient magnetic field Ge for phase-encoding, and a gradient magnetic field Gr for reading out. The gradient magnetic-field power supply 104 supplies a current to the gradient magnetic-field coil 103.

The couch 105 includes a top plate 105a on which the subject P is placed, and the top plate 105a is inserted into a cavity (an imaging port) in the gradient magnetic-field coil 103 in a state with the subject P being placed thereon, under control of the couch control unit 106. Generally, the couch 105 is installed so that a longitudinal direction is parallel to a central axis of the magnetostatic field magnet 101. The couch control unit 106 drives the couch 105 to move the top plate 105a in the longitudinal direction and a vertical direction under control of the computer 130.

The transmission coil 107 is arranged inside the gradient magnetic-field coil 103 to generate a high-frequency magnetic field upon reception of an RF pulse supplied from the transmitting unit 108. The transmitting unit 108 supplies the RF pulse corresponding to a Larmor frequency determined by the type of atoms as a target and the magnetic field intensity to the transmission coil 107.

The reception coil 109 is arranged inside the gradient magnetic-field coil 103 to receive a magnetic resonance signal (hereinafter, "MR signal" where appropriate) issued from the subject P due to an influence of the high-frequency magnetic field. Upon reception of the MR signal, the reception coil 109 outputs the received MR signal to the receiving unit 110.

The transmission coil 107 and the reception coil 109 described above are only examples, and it suffices that the transmission coil 107 is configured by combining one or plural coils, of a coil having only a transmission function, a coil having only a reception function, and a coil having a transmission/reception function.

The receiving unit 110 detects the MR signal output from the reception coil 109, and generates MR data based on the detected MR signal. Specifically, the receiving unit 110 digitally converts the MR signal output from the reception coil 109 to generate the MR data. The receiving unit 110 transmits the generated MR data to the sequence control unit 120. The receiving unit 110 can be provided on a pedestal apparatus side that includes the magnetostatic field magnet 101, the gradient magnetic-field coil 103, and the like.

The sequence control unit 120 drives the gradient magnetic-field power supply 104, the transmitting unit 108, and the receiving unit 110 based on sequence information transmitted from the computer 130 to capture an image of the subject P. The sequence information defines a procedure for performing imaging scan. The intensity of the current to be supplied to the gradient magnetic-field coil 103 and a timing of the current supply by the gradient magnetic-field power supply 104, the intensity of the RF pulse to be supplied to the transmission coil 107, a timing of application of the RF pulse by the transmitting unit 108, and a timing of detecting the MR signal by the receiving unit 110, and the like are defined in the sequence information. For example, the sequence control unit 120 is an integrated circuit such as an ASIC (Application Specific Integrated Circuit) or an FPGA (Field Programmable Gate Array), or an electronic circuit such as a CPU (Central Processing Unit) or an MPU (Micro Processing Unit).

When the MR data is received from the receiving unit 110 as a result of imaging scan of the subject P by driving the gradient magnetic-field power supply 104, the transmitting unit 108, and the receiving unit 110, the sequence control unit 120 transfers the received MR data to the computer 130.

The computer 130 performs the overall control of the MRI apparatus 100, generation of an image, and the like. The computer 130 includes an interface unit 131, a storage unit 132, a control unit 133, an input unit 134, a display unit 135, and an image generating unit 136. The control unit 133 includes an imaging scan condition setting unit 133a and an area deriving unit 133b.

The interface unit 131 transmits the sequence information to the sequence control unit 120, and receives the MR data from the sequence control unit 120. Upon reception of the MR data, the interface unit 131 stores the received MR data in the storage unit 132. The pieces of MR data stored in the storage unit 132 are arranged in a space k by the control unit 133. As a result, the storage unit 132 stores therein space-k data.

The MR data received by the interface unit 131, the space-k data arranged in the space k by the control unit 133, image data generated by the image generating unit 136, and the like are stored in the storage unit 132. For example, the storage unit 132 is a semiconductor memory apparatus such as a RAM (Random Access Memory) or a flash memory, a hard disk, or an optical disk.

The input unit 134 receives various instructions and an information input from an operator. The input unit 134 is, for example, a pointing apparatus such as a mouse or a trackball, a selecting apparatus such as a mode changing switch, or an input apparatus such as a keyboard. The display unit 135 displays a GUI (Graphical User Interface) for receiving an input of imaging scan conditions, an image generated by the image generating unit 136, or the like under control of the control unit 133. The display unit 135 is, for example, a display apparatus such as a liquid crystal display.

The control unit 133 performs the overall control of the MRI apparatus 100 to control imaging scan, generation of an image, display of an image, and the like. For example, the imaging scan condition setting unit 133a receives an input of imaging scan conditions on the GUI, and generates the sequence information according to the received imaging scan conditions. The imaging scan condition setting unit 133a transmits the generated sequence information to the sequence control unit 120. For example, the area deriving unit 133b automatically derives an imaging scan area and a related area thereof (or a candidate thereof) by using the imaging scan conditions received by the imaging scan condition setting unit 133a and the image generated by the image generating unit 136. The control unit 133 is, for example, an integrated circuit such as an ASIC or an FPGA, or an electronic circuit such as a CPU or an MPU. Details of processing performed by the imaging scan condition setting unit 133a and the area deriving unit 133b are described later.

The image generating unit 136 reads the space-k data from the storage unit 132, and performs reconstruction processing such as Fourier transform on the read space-k data to generate an image.

Figure 2:
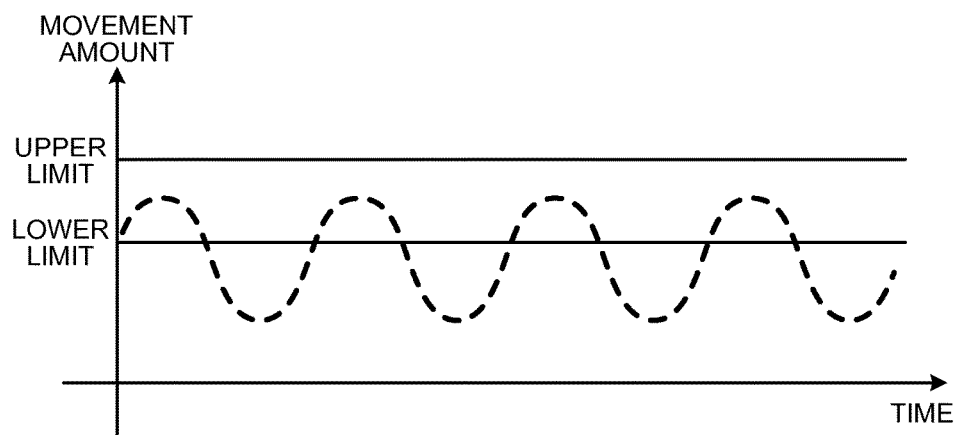
FIG. 2 is an explanatory diagram of imaging scan of a heart in the first embodiment.
Figure 3:
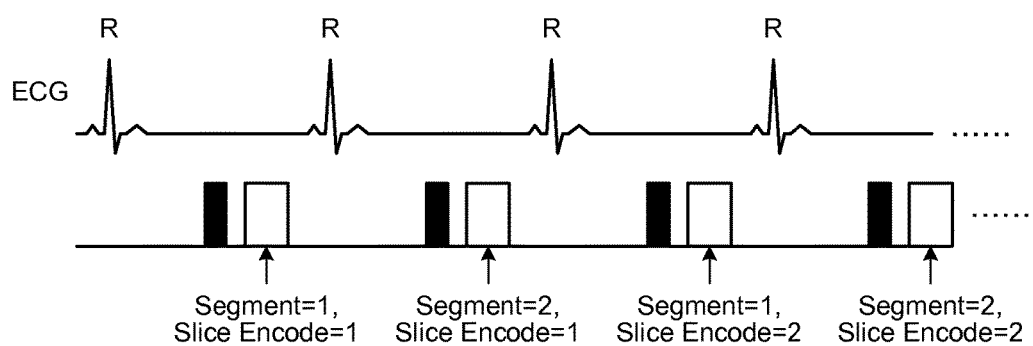
FIG. 3 is an explanatory diagram of imaging scan of a heart in the first embodiment.

FIGS. 2 and 3 are explanatory diagrams of imaging scan of a heart in the first embodiment. In the first embodiment, a respiratory motion is detected, and an imaging scan area including a heart is moved in real time so as to correct a positional deviation of a region to be image-captured caused by the respiratory motion. In the first embodiment, Motion Correction using 1D Motion Probe is used as a correction method thereof.

For example, an application area of a motion detection pulse is set at a top (an apex) of a convex surface of a right diaphragm. The control unit 133 performs one-dimensional Fourier transform on the MR data acquired from the application area. As shown in FIG. 2, a movement amount of the diaphragm is then detected. For example, as shown in FIG. 3, while synchronizing with an electrocardiographic signal (ECG (Electrocardiogram)), the sequence control unit 120 acquires MR data from the application area of the motion detection pulse immediately before acquiring the MR data from the imaging scan area at each heartbeat. In the following explanations, acquisition of the MR data from the imaging scan area is referred to as "actual acquisition", and acquisition of the MR data from the application area of the motion detection pulse is referred to as "Motion Probe acquisition", for convenience sake of explanation. In FIG. 3, a black rectangle indicates the Motion Probe acquisition, and a white rectangle indicates the actual acquisition.

Meanwhile, the control unit 133 performs one-dimensional Fourier transform on the MR data acquired by the Motion Probe acquisition to detect a movement amount of the diaphragm in real time, and estimates a deviation amount in a reading direction, a phase encoding direction, and a slice encoding direction in real time, based on the detected movement amount. When the control unit 133 corrects the position of the imaging scan area in the actual acquisition performed at the same heartbeat based on the estimated deviation amount, the sequence control unit 120 acquires the MR data from the corrected imaging scan area.

In this manner, the sequence control unit 120 acquires all the pieces of MR data required for generating an image, while alternately repeating the Motion Probe acquisition and the actual acquisition. When this imaging scan is performed under free breathing, for example, as shown in FIG. 2, an upper limit and a lower limit are set to the movement amount of the diaphragm, and when a movement outside a threshold range occurs, control such as excluding the MR data acquired by the actual acquisition from an image generation target can be executed. The imaging scan of a heart described above is only an example. For example, the imaging scan can be performed under breath hold, not under free breathing.

Figure 4:
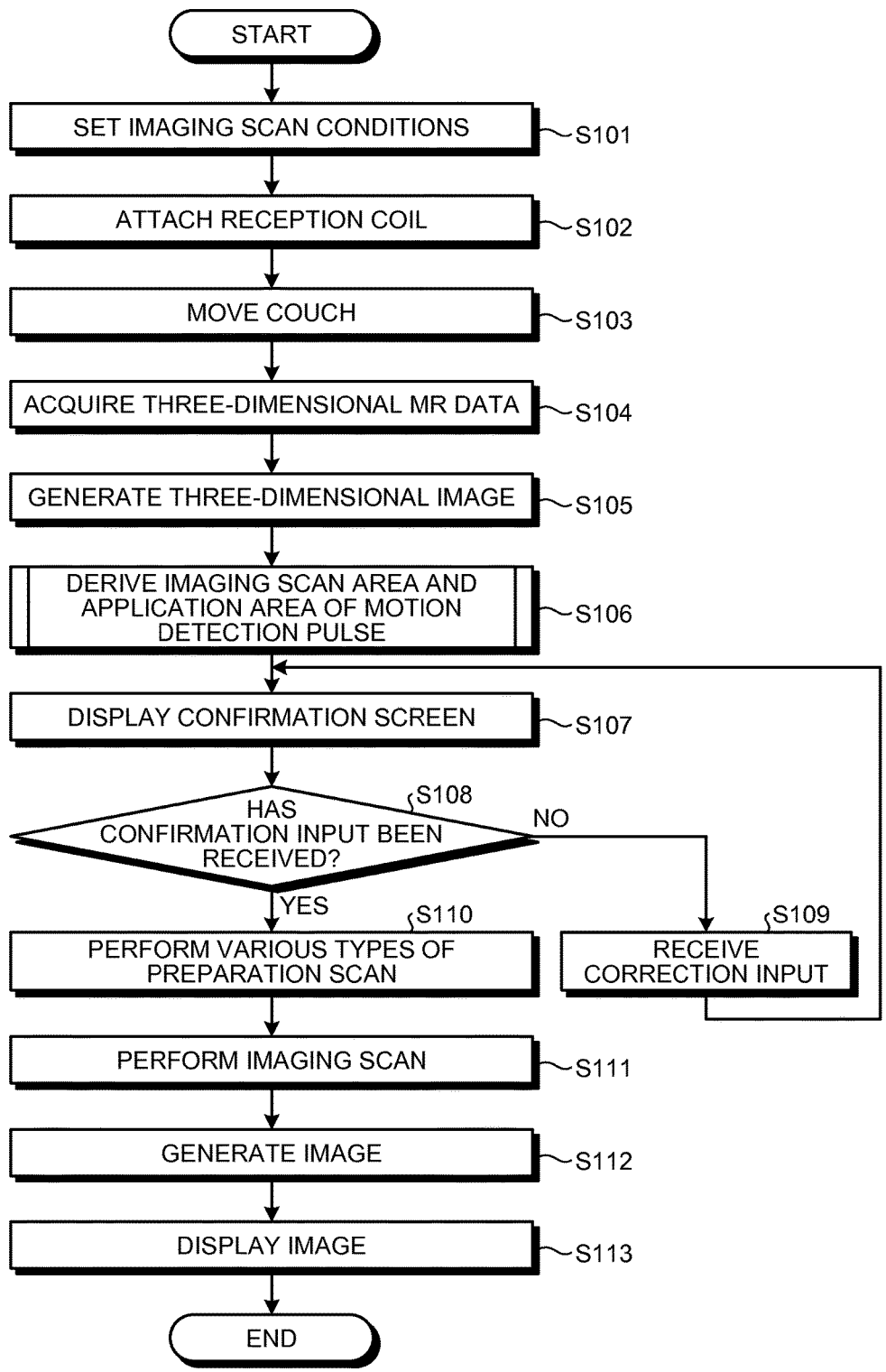
FIG. 4 is a flowchart of a process procedure in the first embodiment.

FIG. 4 is a flowchart of a process procedure of to the first embodiment. The process procedure of the first embodiment is explained with reference to FIGS. 5 to 10.

First, the imaging scan condition setting unit 133a receives an input of imaging scan conditions by an operator on a GUI via the input unit 134 to generate sequence information according to the received imaging scan conditions (Step S101).

Figure 5:
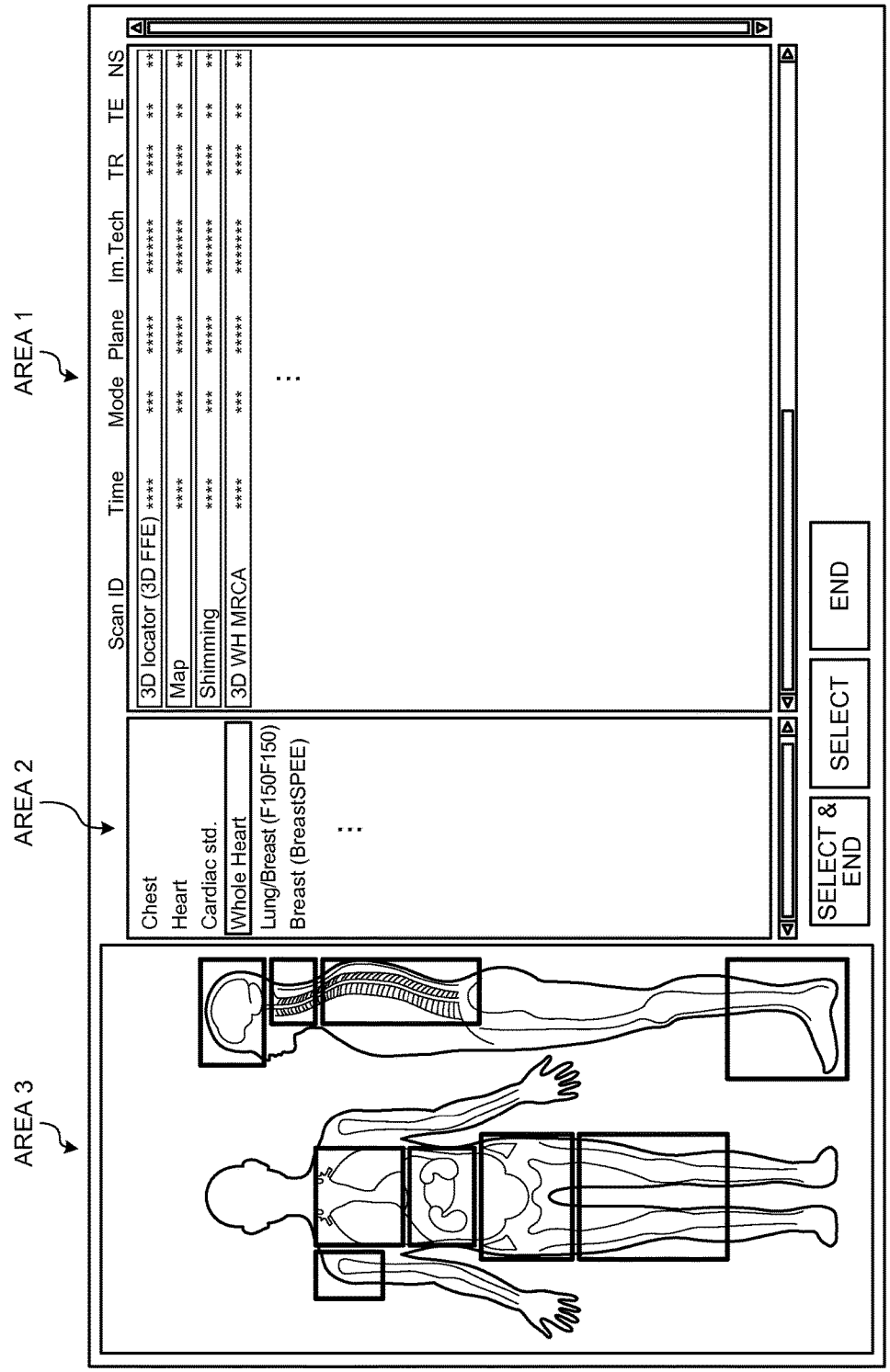
FIG. 5 shows a GUI for inputting imaging scan conditions in the first embodiment.

FIG. 5 shows a GUI for inputting imaging scan conditions in the first embodiment. For example, as shown in FIG. 5, an area 1 for displaying a list of protocols (pulse sequences), an area 2 for displaying a generic term of a group of protocols displayed in the area 1, and an area 3 for receiving selection of each region to be image-captured on a model diagram of human body are displayed on a GUI in order from the right. On such a GUI, for example, an operator can specify a desired protocol group (a pulse sequence group) to be executed by performing selection in the area 3, the area 2, and the area 1 in this order according to a hierarchical structure.

For example, when the operator selects a rectangle corresponding to "chest" in the area 3, a list of generic terms of protocols relating to the "chest" is displayed on the area 2. Subsequently, when the operator selects "Whole Heart", which is a generic term of a group of protocols for imaging the whole heart in the area 2, a list of the group of protocols corresponding to the generic term is displayed in the area 1. In this list, for example, one or plural protocols are included for each of a protocol for acquiring a sensitivity map, a protocol for shimming, and a protocol for imaging. The operator then selects a desired protocol for each of sensitivity mapping, shimming, and imaging from the list displayed in the area 1, and presses an end button. The imaging scan condition setting unit 133a receives specification of the desired protocol group to be executed in this manner, and generates sequence information according to the imaging scan conditions defined in the respective protocols. The GUI shown in FIG. 5 is only an example for convenience sake of explanation, and, for example, the information displayed in each area can be changed arbitrarily according to an operation form.

Referring back to FIG. 4, the reception coil 109 is attached to the subject P, the subject P is placed on the top plate 105a of the couch 105, and the reception coil 109 is electrically connected to the MRI apparatus 100 (Step S102). For example, the reception coil 109 is a body coil having a plurality of coil elements.

Next, the couch control unit 106 moves the couch 105 (Step S103). Specifically, when the couch control unit 106 moves the top plate 105a to a predetermined position, light from a floodlight (not shown) is irradiated to the subject P. An operator inputs the specification of the position of the region to be image-captured via the input unit 134 at a timing at which the light of the floodlight is irradiated to the region to be image-captured (for example, a heart). The couch control unit 106 then moves the top plate 105a so that the specified region to be image-captured is positioned at the center of the magnetic field.

Subsequently, the sequence control unit 120 controls execution of the pulse sequence based on the sequence information to acquire three-dimensional MR data of a range including a heart (Step S104). For example, the sequence control unit 120 acquires the MR data using a GE (Gradient Echo) pulse sequence. Because the GE pulse sequence is a method of applying an excitation pulse of a small flip angle and a gradient pulse, TR (Repetition Time) is short as compared with an SE (Spin Echo) pulse sequence. For example, the sequence control unit 120 acquires the MR data by using 3D FFE (Fast Field Echo).

Figure 6:
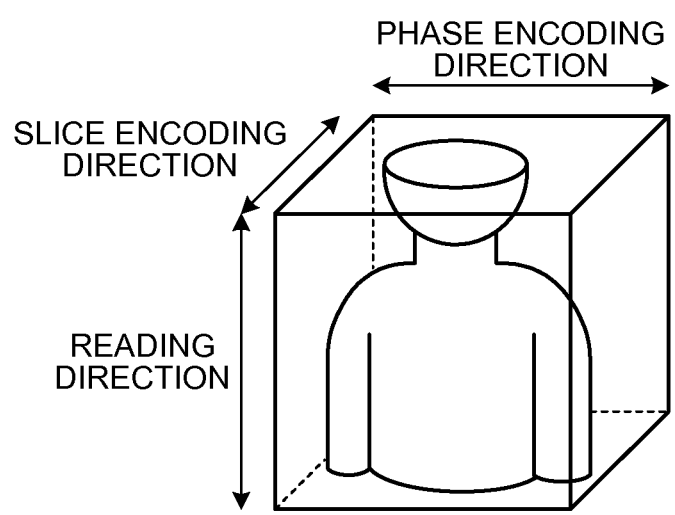
FIG. 6 is an explanatory diagram of three-dimensional MR data in the first embodiment.

FIG. 6 is an explanatory diagram of three-dimensional MR data in the first embodiment. As shown in FIG. 6, for example, the sequence control unit 120 sets a head-feet direction as the reading direction, sets a horizontal direction as the phase encoding direction, and sets a dorsoventral direction as the slice encoding direction to acquire the three-dimensional MR data. The resolution in the head-feet direction can be enhanced by setting the head-feet direction as the reading direction.

For example, the sequence control unit 120 acquires the MR data with the maximum FOV (Field Of View) that can be set by the MRI apparatus 100 (for example, in a range capable of ensuring uniformity of the magnetostatic field intensity), mainly at the center of the magnetic field. As described below, a three-dimensional image generated from the MR data is used for deriving the imaging scan area including a heart and an application area of a motion detection pulse. Therefore, the MR data needs to be acquired in a range including a region used as a landmark in derivation of respective areas. For example, in the first embodiment, it is desired that the MR data is acquired in a range including a heart and the top of the convex surface of a right diaphragm.

The image generating unit 136 generates a three-dimensional image by using the MR data acquired at Step S104 (Step S105). The area deriving unit 133b derives the imaging scan area including a heart and an application area of a motion detection pulse based on the image processing using the three-dimensional image generated at Step S105 (Step S106).

Figure 7:
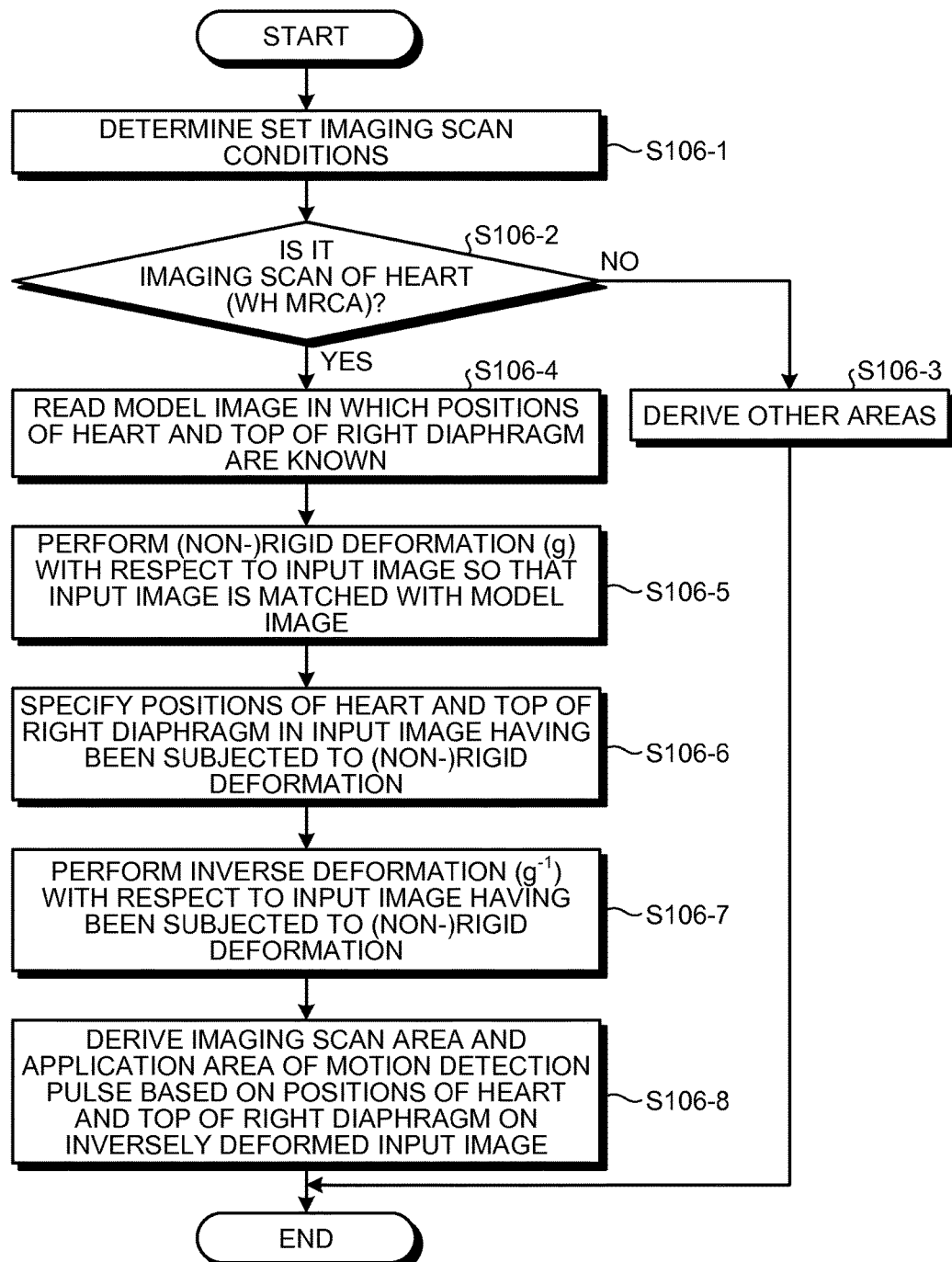
FIG. 7 is a flowchart of a derivation procedure of various areas in the first embodiment.
Figure 8:
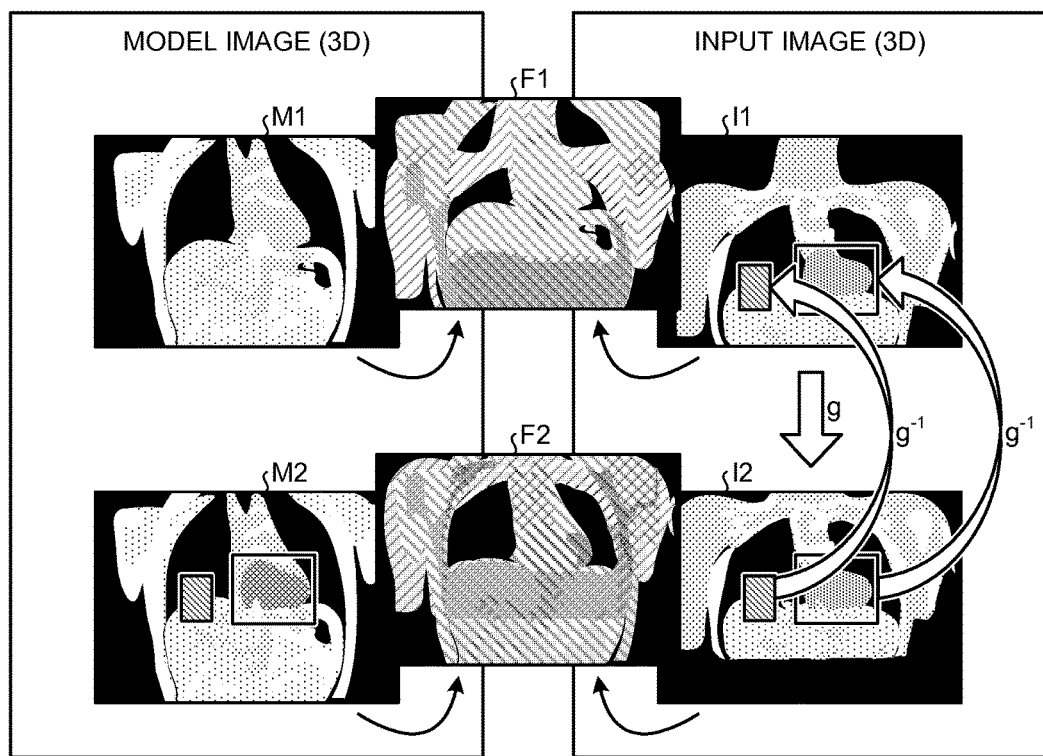
FIG. 8 is an explanatory diagram of derivation of the various areas in the first embodiment.
Figure 9:
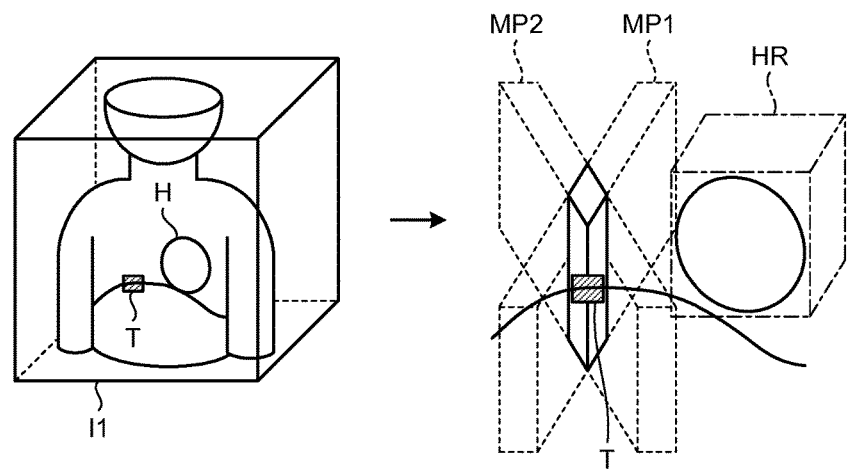
FIG. 9 is an explanatory diagram of derivation of the various areas in the first embodiment.

FIG. 7 is a flowchart of a derivation procedure of various areas in the first embodiment. FIG. 7 corresponds to the process at Step S106 in FIG. 4. FIGS. 8 and 9 are explanatory diagrams of derivation of the various areas in the first embodiment. As shown in FIG. 7, the area deriving unit 133b first determines the imaging scan conditions set at Step S101 in FIG. 4 (Step S106-1). As described below, at the time of deriving the various areas, the area deriving unit 133b needs to read a model image matched with a target thereof and derive the imaging scan area and the related area matched with the target by using the read model image. Therefore, the area deriving unit 133b uses an input of the imaging scan conditions received by the imaging scan condition setting unit 133a to determine the model image to be read and the various areas to be derived. In the first embodiment, the model image is an image (an MR image) acquired by capturing an image of the subject P (for example, a standard patient) in advance by the MRI apparatus 100. The embodiment is not limited thereto, and for example, an average image of images acquired by capturing images of a plurality of patients can be used as the model image. The model image can be an image having been subjected to image processing.

As explained with reference to FIG. 5, for example, an operator can specify the imaging scan conditions in each hierarchy of the area 1, the area 2, and the area 3. Therefore, the area deriving unit 133b can determine the model image to be read and the various areas to be derived by specifying the imaging scan conditions in any of the hierarchies. For example, the area deriving unit 133b can determine the model image to be read and the various areas to be derived based on selection of a rectangle corresponding to the "chest" in the area 3. Furthermore, for example, the area deriving unit 133b can determine the model image to be read and the various areas to be derived based on selection of the generic name of the "Whole Heart" in the area 2. Further, for example, the area deriving unit 133b can determine the model image to be read and the various areas to be derived based on selection of a protocol corresponding to imaging scan of the Whole Heart (for example, a protocol dedicated for the Whole Heart) in the area 1.

The area deriving unit 133b determines, for example, whether it is imaging scan of a heart (WH MRCA) based on any of the imaging scan conditions (Step S106-2). When having determined that it is not imaging scan of a heart (WH MRCA) (NO at Step S106-2), the area deriving unit 133b derives other areas (Step S106-3), and the process is ended.

On the other hand, when having determined that it is the imaging scan of a heart (WH MRCA) (YES at Step S106-2), the area deriving unit 133b reads the model image in which the positions of the heart and the top of the convex surface of the right diaphragm are known from the model images stored in advance (Step S106-4). For example, it is desired to use an image acquired by the same protocol as the protocol (for example, 3D FFE) at the time of acquiring the MR data at Step S104 as the model image. Because contrasts of the images are similar, the accuracy of the image processing using the model image can be enhanced.

In FIG. 8, model images M1 and M2 are the same model images in which positions of a heart and the top of the convex surface of a right diaphragm are known. Meanwhile, an input image I1 is generated at Step S105 in FIG. 4, and an input image I2 is an image in which the image processing of rigid deformation or non-rigid deformation described later is performed with respect to the input image I1. A composite image F1 is a composite image of the model image M1 and the input image I1, and a composite image F2 is a composite image of the model image M2 and the input image I2. The composite images F1 and F2 are for explaining a difference between the two images, and are not used for area derivation performed by the area deriving unit 133b. All the images are three-dimensional images.

Referring back to FIG. 7, the area deriving unit 133b performs image processing (g) such as rigid deformation or non-rigid deformation with respect to the input image so that the input image is matched with the model image (Step S106-5). For example, the area deriving unit 133b solves the following equation (1) to perform registration for obtaining an image deformation parameter.

$$\hat{g} = \underset{g}{\mathrm{argmin}}(E(I(i), M(g(i)))) \qquad (1)$$

In the equation (1), "i" denotes a position vector of an image, "I(i)" is a pixel value of an input image at a position i, and "M(i)" is a pixel value of the model image at the position i. A function "E" is an evaluation function of a similarity between the input image and the model image. The value of the function "E" decreases as the similarity between the input image and the model image increases, and the function "E" is realized by summing square errors between the corresponding pixels. A function "g" is a function of rigid deformation, or non-rigid deformation such as Affine transformation or Thin-Plate-Spline transformation.

For example, FIG. 8 shows a state where the image processing (g) such as rigid deformation or non-rigid deformation is performed with respect to the input image I1 so that the input image I1 is matched with the model image M1 (or the model image M2), and as a result, the input image I2 is acquired. As compared with the composite image F1, the difference between the two images decreases in the composite image F2.

Referring back to FIG. 7, the area deriving unit 133b identifies the positions of the heart and the top of the convex surface of the right diaphragm in an input image having been subjected to rigid deformation or non-rigid deformation (Step S106-6). For example, as shown in FIG. 8, because the positions of the heart and the top of the convex surface of the right diaphragm are known three-dimensionally in the model image M2, the positions of the heart and the top of the convex surface of the right diaphragm can be identified at the same positions also in the input image I2 having been subjected to rigid deformation or non-rigid deformation so that the input image I2 is matched with the model image M2. The position of the top can be identified by a point, or can be identified by an area having a certain range.

Subsequently, the area deriving unit 133b performs image processing ($g^{-1}$) to inversely deform the input image having been subjected to rigid deformation or non-rigid deformation to the original input image (Step S106-7). Accordingly, as shown in FIG. 8, the area deriving unit 133b can identify the positions of the heart and the top of the convex surface of the right diaphragm on the inversely deformed input image I1. Therefore, the area deriving unit 133b derives the imaging scan area including the heart and the application area of the motion detection pulse based on these positions (Step S106-8).

For example, when having identified the position of "heart" by the image processing using the model image, the area deriving unit 133b derives "heart area" including the "heart", and derives an "imaging scan area including the heart" that includes the derived "heart area". The method mainly assumes a case where the size of the "heart" directly derived from the model image is different from the size of the "heart area" (the "heart area" is larger than the "heart"). As described below, because the application area of the motion detection pulse is preferably set not to overlap on the heart, it is possible to avoid more reliably that the application area of the motion detection pulse overlaps on the heart, by deriving a large "heart area" to some extent.

When having identified the position of "the top of the convex surface of the right diaphragm" by the image processing using the model image, the area deriving unit 133b derives the "application area of the motion detection pulse" based on "the top of the convex surface of the right diaphragm". According to such processing, the area deriving unit 133b derives at least one of the position, the size, and the direction of the imaging scan area including the heart and the application area of the motion detection pulse. This point is explained below in detail.

For example, the area deriving unit 133b defines the size of the heart area and the size of the application area of the motion detection pulse in advance, to set an area having a pre-defined size so as to include the region to be image-captured and other landmarks, which are identified on the input image I1.

For example, as shown in FIG. 9, a heart H as the region to be image-captured and the top T of the convex surface of the right diaphragm as other landmarks are identified on the input image I1. Meanwhile, as shown in FIG. 9, the size of a cuboid is pre-defined for a heart area HR and application areas MP1 and MP2 of the motion detection pulse. In the first embodiment, a crossing method of two surfaces that excites a square pillar area by crossing an excitation pulse and a refocusing pulse in an SE method is adopted as an application method of the motion detection pulse. Therefore, MP1 and MP2 are the application areas of the motion detection pulse.

Therefore, for example, the area deriving unit 133b sets the cuboid heart area HR having the pre-defined size so as to include the heart identified on the inversely deformed input image I1. Furthermore, for example, the area deriving unit 133b sets the cuboid application areas MP1 and MP2 having the pre-defined size so that the top T of the convex surface of the right diaphragm is positioned at the center of the crossing square pillar area (expressed by a solid line in FIG. 9).

At this time, the area deriving unit 133b adjusts the crossing condition, that is, the direction of the application areas MP1 and MP2 so that the application areas MP1 and MP2 do not overlap on the heart area HR. This is because, as described above, the MR data is acquired from the application areas of the motion detection pulse immediately before the MR data is acquired from the imaging scan area including the heart, and thus if the application areas overlaps on the heart, an artifact may occur in an image of the heart due to a relation with recovery of longitudinal magnetization. Because the area deriving unit 133b ascertains the position of the heart on the three-dimensional image, such setting is possible.

Furthermore, after having derived the heart area HR, the area deriving unit 133b derives the imaging scan area from which the MR data is actually acquired, so as to include the heart area HR. The imaging scan area is derived not only to include the heart area HR, but also with a sufficient size, taking folding back of the image and the like into consideration. The size of the imaging scan area is also preset.

An example in which the size of the heart area, the size of the application areas of the motion detection pulse, and the size of the imaging scan area are pre-defined has been explained above. However, the embodiment is not limited thereto. For example, the area deriving unit 133b can adjust the size and the direction of various areas appropriately, based on the information such as the size of the heart identified on the input image and the distance between the top of the convex surface of the right diaphragm and the heart. Furthermore, for example, the area deriving unit 133b can set the cuboid various areas themselves on the model image. In this case, it is considered that the various areas cannot maintain the cuboid shape in the process of inverse deformation. However, after the inverse deformation, the area deriving unit 133b can form the various areas into the cuboid shape. For example, in the method described above, a method of performing two-stage procedures such that the position of the "heart" is identified from the model image and then the "heart area HR" is derived has been explained; however, the embodiment is not limited thereto. For example, the area deriving unit 133b can derive the "heart area HR" directly by image processing using the model image. Further, for example, the area deriving unit 133b can derive the application areas MP1 and MP2 of the motion detection pulse directly by image processing using the model image.

In this manner, the imaging scan area including the heart and the application areas of the motion detection pulse are derived by the area deriving unit 133b. Referring back to FIG. 4, the area deriving unit 133b then displays a confirmation screen for an operator to confirm the various areas derived by the area deriving unit 133b on the display unit 135 (Step S107).

Figure 10:
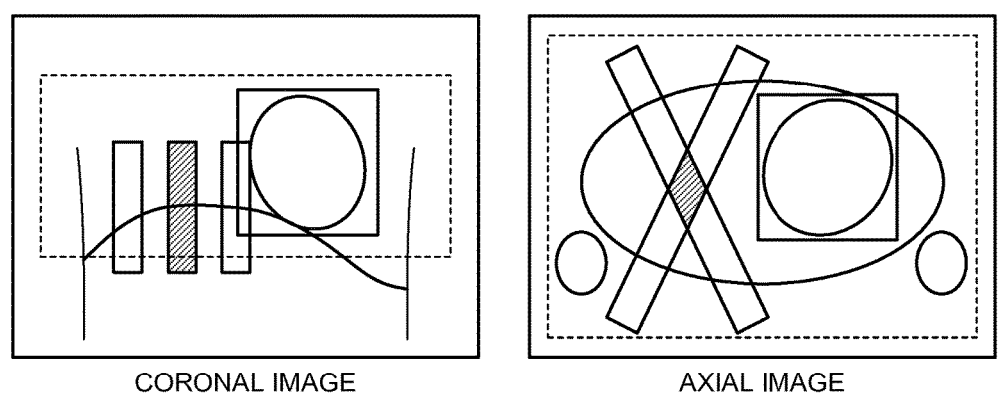
FIG. 10 is an explanatory diagram of a confirmation screen in the first embodiment.

FIG. 10 is an explanatory diagram of a confirmation screen in the first embodiment. The area deriving unit 133b generates a coronal image and an axial image, which are two-dimensional cross-sectional images, for example, from the MR data acquired at Step S104. The area deriving unit 133b displays, as shown in FIG. 10, the imaging scan area including a heart (expressed by a dotted line in FIG. 10), the heart area HR, the application areas MP1 and MP2, and the crossing area of the two application areas (expressed by hatching in FIG. 10) derived at Step S106 on the generated coronal image and axial image, respectively. An operator can correct the imaging scan area including the heart, the heart area HR, and the application areas MP1 and MP2 appropriately on the confirmation screen. As is obvious in FIG. 10, the imaging scan area itself is set to be sufficiently larger than the heart area HR. For example, in the coronal image in FIG. 10, it is understood that the imaging scan area is set with a larger width than the width of the body of the subject P. Furthermore, in the axial image in FIG. 10, it is understood that the imaging scan area is set with a size including the body of the subject P.

Referring back to FIG. 4, the area deriving unit 133b determines whether a confirmation input has been received (Step S108). When the confirmation input has not been received (NO at Step S108), the area deriving unit 133b receives a correction input on the confirmation screen (Step S109), and displays the confirmation screen again (Step S107). On the other hand, when the confirmation input has been received (YES at Step S108), the sequence control unit 120 subsequently performs various types of preparation scan (Step S110).

For example, the preparation scan include scan for acquiring profile data indicating the sensitivity of each coil element (or each channel) in an array direction, scan for acquiring sensitivity maps indicating the sensitivity distribution of each coil element (or each channel), scan for acquiring spectrum data for obtaining a center frequency of the RF pulse, and scan for obtaining a current value that is caused to flow in a correction coil (not shown) in order to adjust the uniformity of the magnetostatic field. The sensitivity maps generally need only to be acquired before starting an image generation process, the sensitivity maps do not need to be acquired prior to the imaging scan.

The sequence control unit 120 then sets the imaging scan area and the application areas of the motion detection pulse, which are derived at Step S106 and confirmed at Step S108, and executes the imaging scan in which the Motion Probe acquisition and the actual acquisition are alternately repeated (Step S111).

Thereafter, the image generating unit 136 generates an image from the MR data acquired by the sequence control unit 120 (Step S112) and displays the generated image on the display unit 135 (Step S113).

As described above, according to the first embodiment, the imaging scan area and the application areas of the motion detection pulse can be automatically derived from the three-dimensional MR data acquired prior to the imaging scan. Therefore, various areas can be set easily and in a short time. Furthermore, according to the first embodiment, because the positional relation between the areas can be adjusted and derived so that the application areas of the motion detection pulse and the heart do not overlap on each other, areas required for imaging scan can be derived in a consistent and highly accurate manner.

Further, according to the first embodiment, because the model image or the like to be used for the area derivation is determined according to the imaging scan conditions input from an operator, processes until the area derivation can be performed continuously without performing any additional operation for the area derivation. Further, according to the first embodiment, because the confirmation screen of various areas derived automatically is displayed and correction is received from the operator, for example, even more detailed demands for each individual test can be handled.

(Modification of First Embodiment)

Embodiments are not limited to the first embodiment described above.

For example, in the first embodiment, application areas of a motion detection pulse are obtained by designating the top of the convex surface of a right diaphragm as a landmark. However, the embodiment is not limited thereto. For example, the application areas of the motion detection pulse can be obtained by detecting a left diaphragm (a cardiac apex side) as the landmark. In this case, for example, the area deriving unit 133b can obtain a plurality of candidates of the application areas, display the candidates on the confirmation screen, and receive selection by an operator. Furthermore, for example, the area deriving unit 133b can determine more appropriate application areas and can display only the most appropriate application area on the confirmation screen or can display the application areas with a priority order. This determination can be performed, for example, based on an overlapping condition on a heart and the like. The contents described above such as obtaining the plurality of candidates can be similarly applied to other embodiments.

For example, in the first embodiment described above, the crossing method of two surfaces has been explained as the application method of the motion detection pulse. However, the embodiment is not limited thereto, and for example, a pencil beam method used in the GE pulse sequence can be used.

For example, in the first embodiment described above, Motion Correction using 1D Motion Probe has been explained as the correction method of a positional deviation of the region to be image-captured caused by a respiratory motion. However, the embodiment is not limited thereto, and for example, Motion Correction using 2D Motion Probe can be used. According to the 2D Motion Probe, two-dimensional Fourier transform is applied on the MR data acquired by the Motion Probe acquisition, and the movement amount in a vertical direction and a front-back direction of the diaphragm is detected based on the imaged data. In this case, cross section setting of the 2D Motion Probe can be set, for example, as a 2D horizontal cross section, using a line in a body-axis direction passing through a position (a point) of the identified top of the diaphragm as an axis. Alternatively, because the positions of vital organs or a vascular system have been identified, cross section setting can be performed at an angle for avoiding the vital organs or the like, using the line in the body-axis direction passing through the position (the point) of the top of the diaphragm as an axis.

In the embodiment of the first embodiment, a heart is assumed as the region to be image-captured. However, the embodiment is not limited thereto, and other regions to be image-captured can be used. For example, a case where the 2D Motion Probe is used in a DWI (Diffusion Weighted Image) test of an abdominal region can be assumed.

Figure 11:
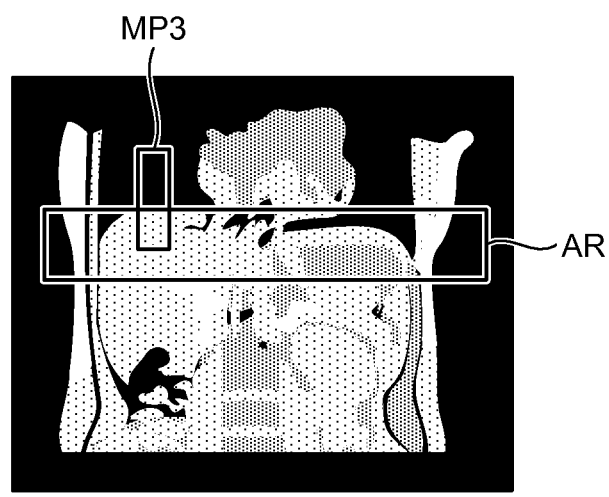
FIG. 11 is an explanatory diagram of a modification of the first embodiment.

FIG. 11 is an explanatory diagram of a modification of the first embodiment. As shown in FIG. 11, in the DWI test of the abdominal region, for example, an application area MP3 of the motion detection pulse is set at the top position of the convex surface of a right diaphragm together with the imaging scan area AR of the abdominal region. The application areas of the motion detection pulse are the same as those in the first embodiment; however, because 2D PACE is used, the width tends to be wider. The process performed by the area deriving unit 133b is the same as that in the first embodiment. That is, the area deriving unit 133b reads the model image matched with the target according to determination based on the input imaging scan conditions, and uses the read model image to derive the imaging scan area of the abdominal region matched with the target and the application areas of the motion detection pulse. In this case, as a landmark, for example, a diaphragm, a liver, a heart, spines, or other vascular systems can be appropriately selected or combined to be used.

(Second Embodiment)

A second embodiment is explained next. In the second embodiment, imaging scan of a portal vein by a Time-SLIP is explained. The MRI apparatus 100 according to the second embodiment has the same configuration (see FIG. 1) as that of the first embodiment, and performs same process procedures as those in the first embodiment (see FIG. 4).

The Time-SLIP is briefly explained first. In the Time-SLIP, fluid flowing into an imaging scan area or flowing out to the imaging scan area is labeled in a labeled area (an application area of a tag pulse) independent of the imaging scan area. The labeled area is set, for example, in an upstream of a fluid channel. Accordingly, a signal value of the fluid flowing into the imaging scan area or flowing out to the imaging scan area after a predetermined time becomes relatively high or low, and the fluid is drawn. The predetermined time may be referred to as "BBTI (Black-Blood Time to Inversion) time" or the like.

For example, when a predetermined delay time has passed since a peak of an R-wave of an electrocardiac signal, the sequence control unit 120 applies an area non-selective inversion pulse and an area selective inversion pulse as the tag pulse. Generally, the area non-selective inversion pulse is applied to the whole imaging scan area and the area selective inversion pulse is applied to the labeled area. The presence of application of the area non-selective inversion pulse can be selected according to how the signal is drawn.

A typical example thereof is explained. For example, a case where the labeled area is set in an imaging scan area is assumed. First, when the sequence control unit 120 applies the area non-selective inversion pulse to the whole imaging scan area, longitudinal magnetization components of tissues in the whole imaging scan area are inverted. Subsequently, the sequence control unit 120 applies the area selective inversion pulse only to the labeled area in the imaging scan area. The longitudinal magnetization components of the tissues in the labeled area are then inverted again. After the BBTI time has passed since the application, the tissues applied with only the area non-selective inversion pulse, that is, the tissues other than the labeled tissues are recovered, and the longitudinal magnetization components thereof become zero (a Null Point). The sequence control unit 120 acquires an MR signal, for example, at this timing. As a result, only the labeled fluid is visualized with a high signal value. Because the labeled fluid flows out to the imaging scan area, it may be referred to as "flow-out" or the like.

Meanwhile, a case where the labeled area is set outside an imaging scan area is assumed. When the sequence control unit 120 applies the area selective inversion pulse only to the labeled area outside the imaging scan area, the longitudinal magnetization components of the tissues in the labeled area are inverted. Thereafter, the labeled fluid flows into the imaging scan area. However, because the tissues in the imaging scan area have not been applied with the inversion pulse, there is a difference between the longitudinal magnetization components in the labeled area and the imaging scan area. The sequence control unit 120 acquires an echo signal after the BBTI time. As a result, only the labeled fluid is visualized with a low signal value. Because the labeled fluid flows into the imaging scan area, it may be referred to as "flow-in" or the like.

In the Time-SLIP, a desired target can be selectively drawn not only in the typical example described above, but also by appropriately combining the setting method of the labeled area, the presence of application of the area non-selective inversion pulse, and the like.

Also in the second embodiment, the whole process is performed according to the process procedure (see FIG. 4) same as that of the first embodiment. That is, also in the second embodiment, the imaging scan condition setting unit 133*a* first receives an input of the imaging scan conditions on a GUI, and generates sequence information according to the received imaging scan conditions. Subsequently, the reception coil 109 is attached to the subject P, and the couch control unit 106 moves the couch 105. At this time, an operator inputs specification of the position of the region to be image-captured (for example, the abdominal region) at a timing when light of a floodlight is irradiated to the region to be image-captured. The couch control unit 106 then moves the top plate 105*a* so that the specified region to be image-captured is positioned at the center of the magnetic field.

Subsequently, the sequence control unit 120 controls execution of the pulse sequence based on the sequence information, thereby acquiring three-dimensional MR data with the maximum FOV that can be set by the MRI apparatus 100 mainly at the center of the magnetic field. The image generating unit 136 then generates a three-dimensional image by using the acquired MR data, and the area deriving unit 133*b* derives the imaging scan area of the abdominal region and the application area of the tag pulse based on image processing using the generated three-dimensional image. Derivation of various areas by the area deriving unit 133*b* is described later.

Thereafter, the area deriving unit 133*b* receives confirmation by displaying the confirmation screen for an operator to confirm the various areas, the sequence control unit 120 executes various types of preparation scan, and imaging scan (for example, 3D SSFP (Steady-State Free Precession) or 3D FFE), and the image generating unit 136 generates and displays the image.

Figure 12:
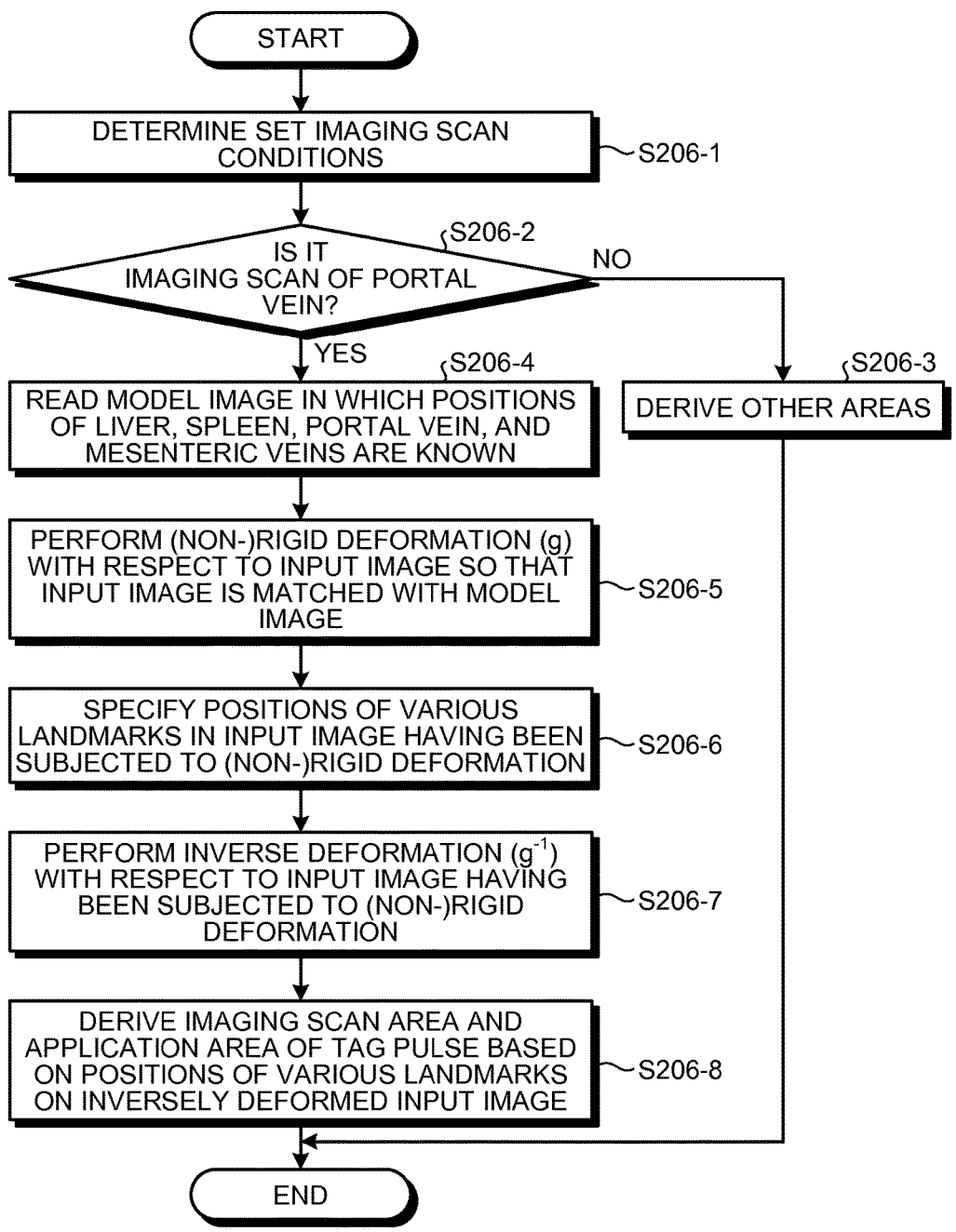
FIG. 12 is a flowchart of a derivation procedure of various areas in a second embodiment.

FIG. 12 is a flowchart of a derivation procedure of various areas in the second embodiment. As shown in FIG. 12, the area deriving unit 133*b* first determines the imaging scan conditions set at Step S101 in FIG. 4 as in the first embodiment (Step S206-1).

Figure 13:
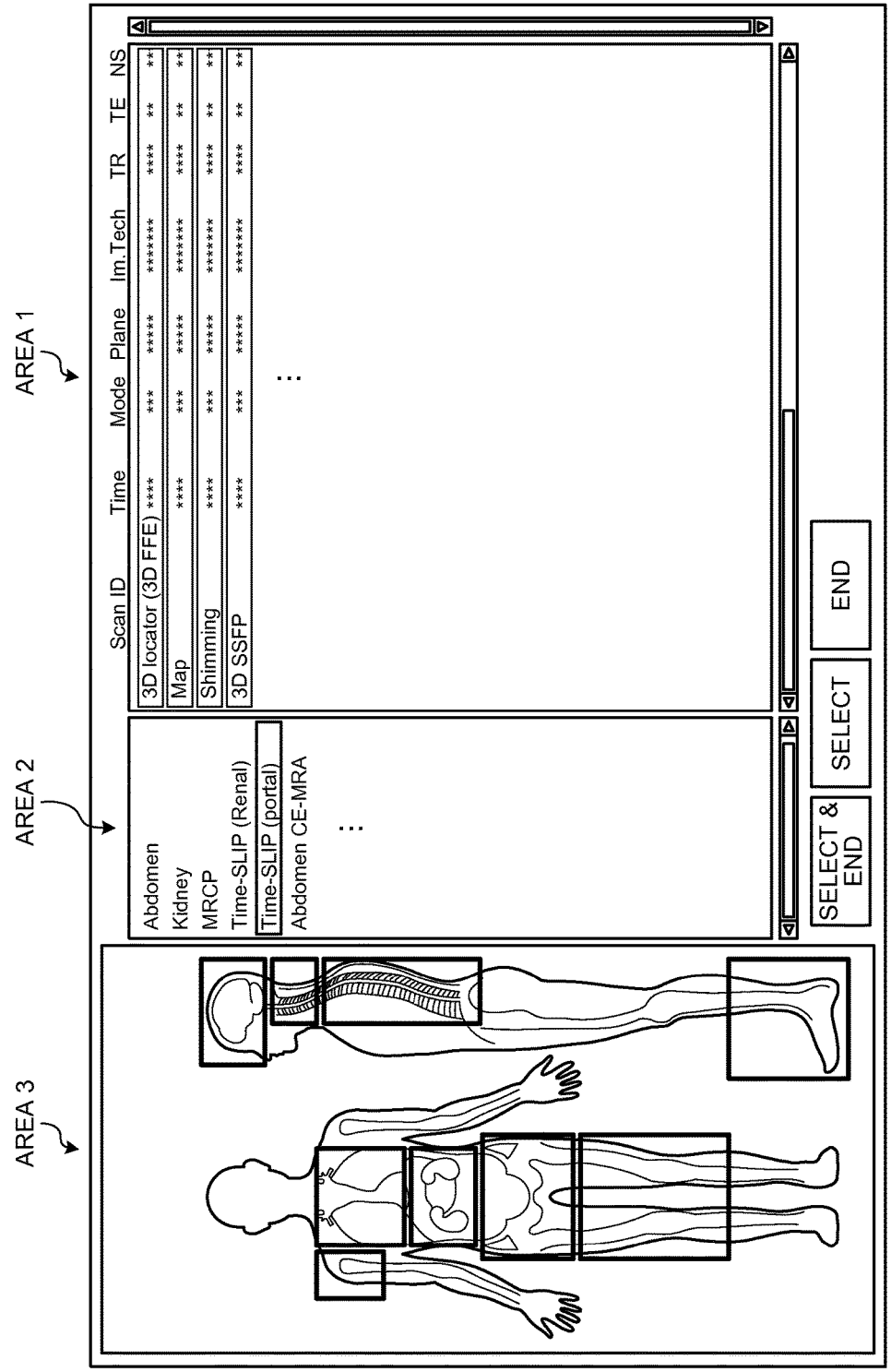
FIG. 13 shows a GUI for inputting imaging scan conditions in the second embodiment.

FIG. 13 shows a GUI for inputting the imaging scan conditions in the second embodiment. For example, the area deriving unit 133*b* can determine a model image to be read and various areas to be derived based on selection of a rectangle corresponding to the "abdominal region" in the area 3. Furthermore, for example, the area deriving unit 133*b* can determine the model image to be read and various areas to be derived based on selection of the "Time-SLIP (portal)", which is the generic name of a group of protocols for capturing an image of the portal vein by using the Time-SLIP, in the area 2. Further, for example, the area deriving unit 133*b* can determine the model image to be read and various areas to be derived based on selection of a protocol corresponding to imaging scan of the portal vein using the Time-SLIP (for example, a protocol dedicated for capturing the image of the portal vein using the Time-SLIP) in the area 1.

The area deriving unit 133*b* determines, for example, whether the image of the portal vein is to be captured by using the Time-SLIP based on any of the imaging scan conditions (Step S206-2). When having determined that the image of the portal vein is not to be captured by using the Time-SLIP (NO at Step S206-2), the area deriving unit 133b performs a deriving process of other areas (Step S206-3), and the process is ended.

Figure 14:
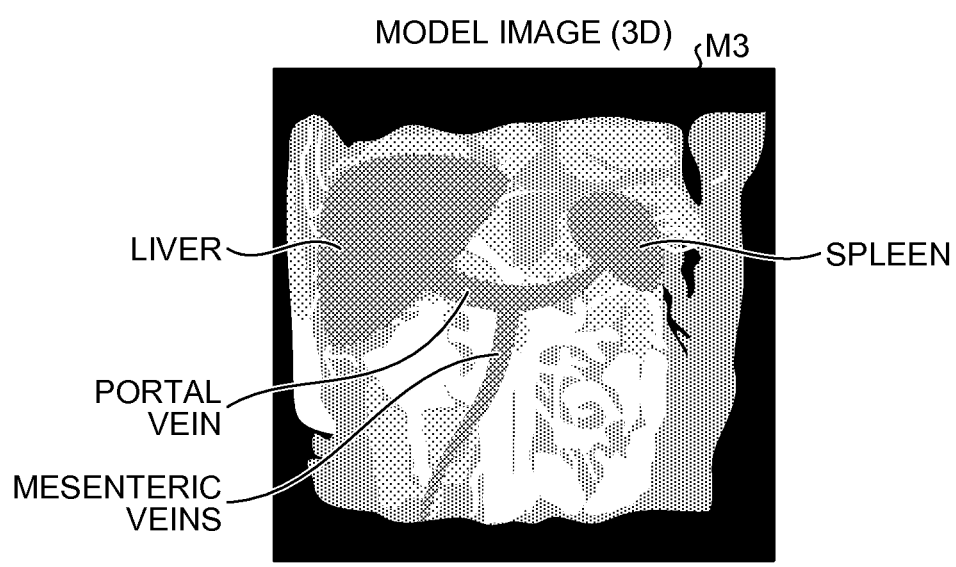
FIG. 14 is an explanatory diagram of a model image in the second embodiment.

On the other hand, when having determined that the image of the portal vein is to be captured by using the Time-SLIP (YES at Step S206-2), the area deriving unit 133b reads a model image in which the positions of the liver, the spleen, and the portal vein and the mesenteric veins as the vascular system are known from the pre-stored model images (Step S206-4). FIG. 14 is an explanatory diagram of a model image in the second embodiment. As shown in FIG. 14, in the second embodiment, the positions of the liver, the spleen, and the portal vein and the mesenteric vein as the vascular system (for example, a bifurcation between the portal vein and the mesenteric veins) are known.

Referring back to FIG. 12, the area deriving unit 133b performs the image processing (g) such as rigid deformation or non-rigid deformation with respect to the input image so that the input image is matched with the model image (Step S206-5), as in the first embodiment.

Subsequently, the area deriving unit 133b identifies the positions of the liver, the spleen, and the portal vein and the mesenteric vein as the vascular system (for example, the bifurcation between the portal vein and the mesenteric veins) in the input image having been subjected to rigid deformation or non-rigid deformation (Step S206-6). For example, as shown in FIG. 14, because the positions of the liver, the spleen, and the portal vein and the mesenteric vein as the vascular system are known three-dimensionally in a model image M3, these positions can be identified at the same positions also in the input image having been subjected to rigid deformation or non-rigid deformation, so that the input image is matched with the model image M3.

Subsequently, the area deriving unit 133b performs image processing ($g^{-1}$) to inversely deform the input image having been subjected to rigid deformation or non-rigid deformation to the original input image (Step S206-7). Subsequently, the area deriving unit 133b can identify the positions of the liver, the spleen, and for example, the bifurcation between the portal vein and the mesenteric veins on the inversely deformed input image. Therefore, the area deriving unit 133b derives the imaging scan area and the application area of the tag pulse based on these positions (Step S206-8).

Figure 15:
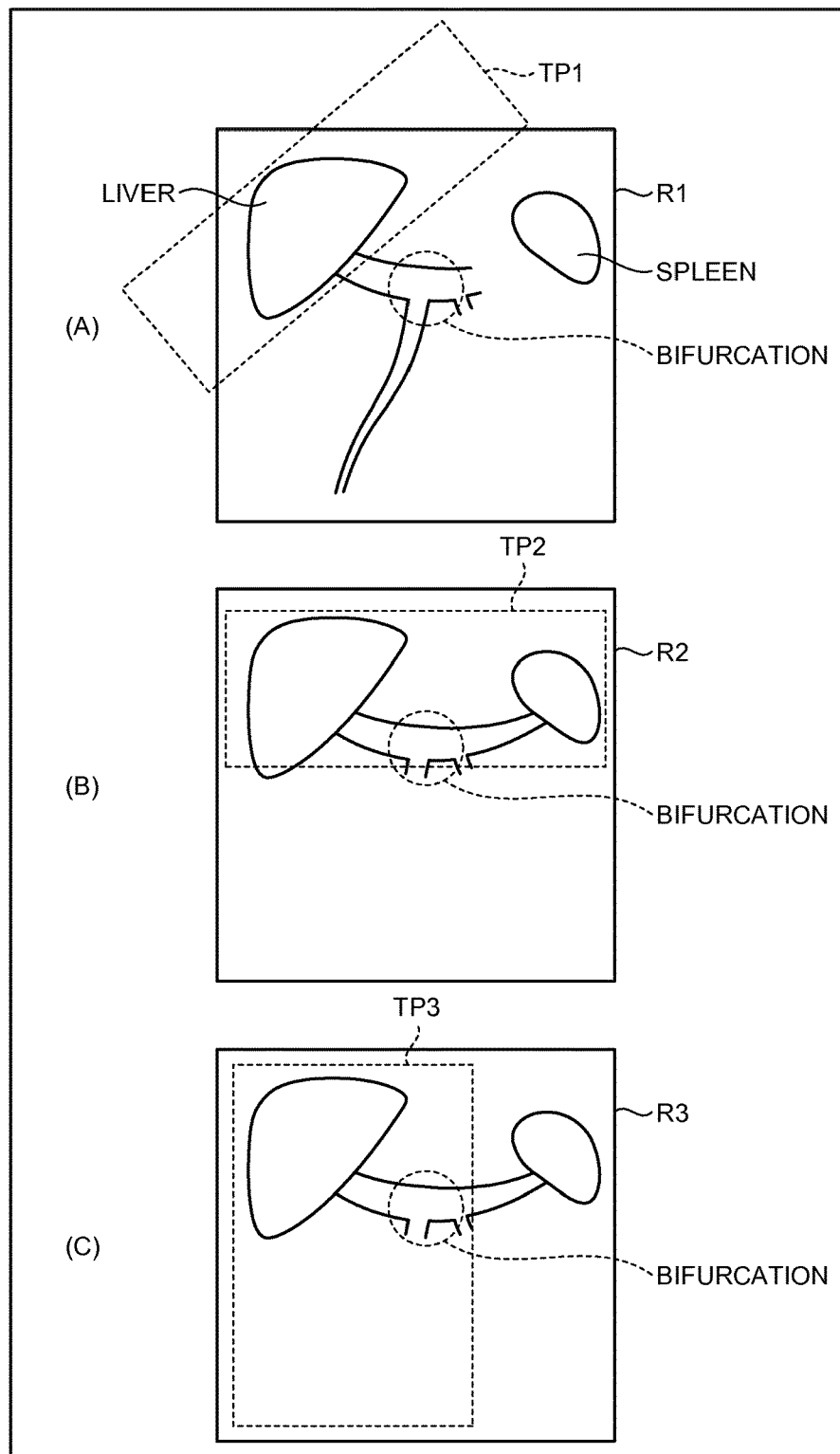
FIG. 15 is an explanatory diagram of an imaging scan area and an application area of a tag pulse in the second embodiment.

FIG. 15 is an explanatory diagram of an imaging scan area and an application area of a tag pulse in the second embodiment. First, in the second embodiment, a cube having a size including the liver and the spleen is set as the imaging scan area. Furthermore, in the second embodiment, as the application area of the tag pulse, a first pattern in which blood flowing into the portal vein is imaged, a second pattern in which only blood flowing from the mesenteric vein to the portal vein is imaged, and a third pattern in which only blood flowing from the splenic vein to the portal vein is imaged are respectively set. The embodiment is not limited to the example shown in FIG. 14. The imaging scan area and the application area of the tag pulse can be changed arbitrarily according to a target to be imaged, how the target is drawn (for example, whether the target is drawn in black blood or bright blood), or the like.

For example, as shown in (A) in FIG. 15, the area deriving unit 133b sets a cubic area having a size including the liver and the spleen as an imaging scan area R1 based on the positions of the liver and the spleen identified on the input image. Further, for example, the area deriving unit 133b identifies the position of the bifurcation between the portal vein and the mesenteric veins on the input image, and sets an application area TP1 of the tag pulse of a cuboid having a predetermined size, while being placed obliquely with an inclination following the inclination of a lower edge of the liver, on the side closer to the liver than the identified bifurcating position.

For example, in the case of the first pattern shown in (A) in FIG. 15, by inverting longitudinal magnetization in the application area TP1 of the tag pulse and acquiring MR signals in the imaging scan area R1 after a predetermined time (at the time when a blood signal in the liver other than the portal vein becomes a null point), the blood flowing into the portal vein can be selectively drawn.

For example, as shown in (B) in FIG. 15, the area deriving unit 133b sets a cubic area having a size including the liver and the spleen as an imaging scan area R2, based on the positions of the liver and the spleen identified on the input image. For example, the area deriving unit 133b identifies the position of the bifurcation between the portal vein and the mesenteric veins and sets a cuboid application area TP2 of the tag pulse having the size set in advance on the input image, placed transversely on an upper side including the identified bifurcating position.

For example, in the case of the second pattern shown in (B) in FIG. 15, by inverting longitudinal magnetization in the application area TP2 of the tag pulse and acquiring MR signals in the imaging scan area R2 after a predetermined time (at the time when a blood signal in the liver other than the portal vein becomes a null point), the blood flowing from the mesenteric vein into the portal vein can be selectively drawn.

For example, as shown in (C) in FIG. 15, the area deriving unit 133b sets a cubic area having a size including the liver and the spleen as an imaging scan area R3, based on the positions of the liver and the spleen identified on the input image. For example, the area deriving unit 133b identifies the position of the bifurcation between the portal vein and the mesenteric veins and sets a cuboid application area TP3 of the tag pulse having the size set in advance on the input image, placed longitudinally on the left side including the identified bifurcating position.

For example, in the case of the second pattern shown in (C) in FIG. 15, by inverting longitudinal magnetization in the application area TP3 of the tag pulse and acquiring MR signals in the imaging scan area R3 after a predetermined time (at the time when a blood signal in the liver other than the portal vein becomes a null point), the blood flowing from the splenic vein into the portal vein can be selectively drawn.

An example in which the size of the application area of the tag pulse is predetermined has been explained above; however, the embodiment is not limited thereto. For example, the area deriving unit 133b can adjust the position, the size, and the direction of various areas appropriately based on the information such as the size of the liver and the distance between the liver and the spleen identified on the input image. Further, for example, the area deriving unit 133b can set cuboid various areas themselves on the model image. In this case, it is considered that the various areas cannot maintain the cuboid shape in the process of inverse deformation. However, after the inverse deformation, the area deriving unit 133b can fix the cuboid shape.

Figure 16:
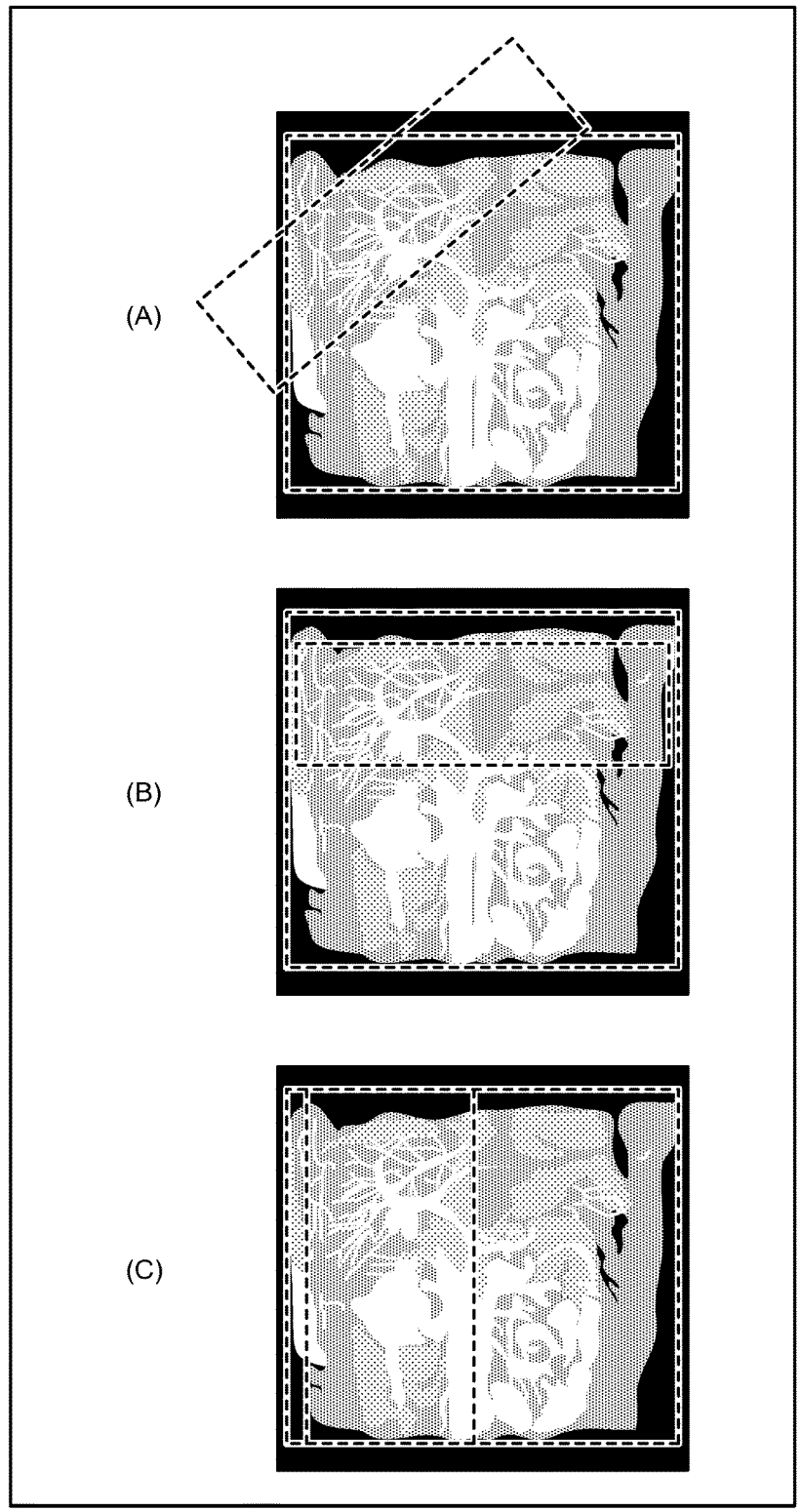
FIG. 16 is an explanatory diagram of a confirmation screen in the second embodiment.

FIG. 16 is an explanatory diagram of the confirmation screen in the second embodiment. The area deriving unit 133b generates a coronal image and an axial image, which are two-dimensional cross-sectional images, for example, from the MR data acquired at Step S104. The area deriving unit 133b displays the imaging scan areas R1 to R3 of the portal vein and the application areas TP1 to TP3 of the tag pulse derived at Step S206 on the generated coronal image and axial image, respectively. In FIG. 16, only the coronal image is exemplified. An operator can correct the imaging scan areas R1 to R3 of the portal vein and the application areas TP1 to TP3 of the tag pulse appropriately on the confirmation screen.

Figure 17:
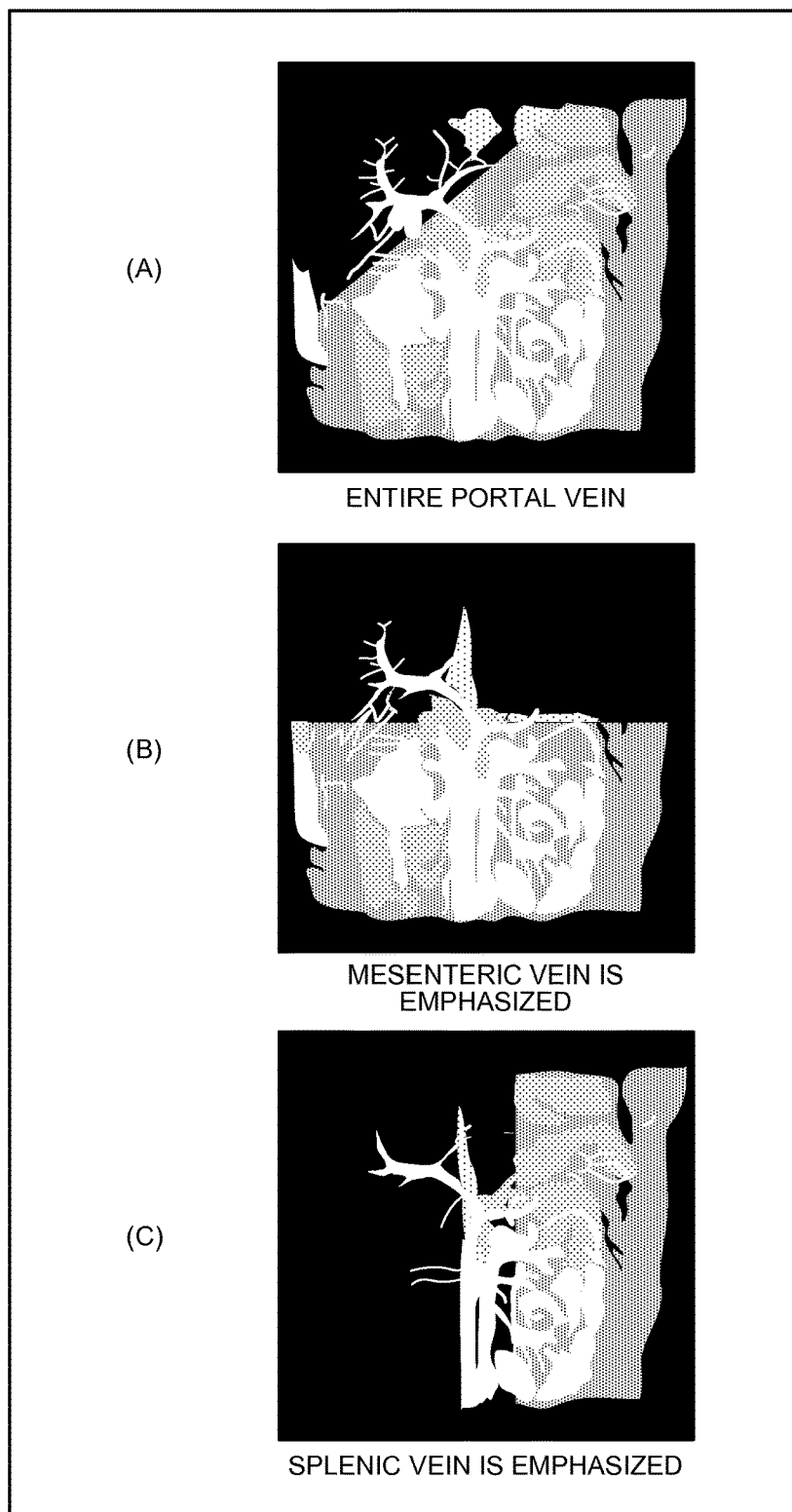
FIG. 17 is an example of an image generated in the second embodiment.

FIG. 17 is an example of the image generated in the second embodiment. As shown in FIG. 17, in the application area of the tag pulse, although a signal drop is recognized as a whole, blood flowing into the application area is drawn in bright blood.

As described above, according to the second embodiment, the imaging scan area of the portal vein and the application area of the tag pulse can be automatically derived from three-dimensional MR data acquired prior to the imaging scan. Accordingly, various areas can be set easily and in a short time.

Furthermore, according to the second embodiment, because the model image or the like to be used for the area derivation is determined according to the imaging scan conditions input from an operator, processes until the area derivation can be performed continuously without performing any additional operation for the area derivation. Further, according to the second embodiment, because the confirmation screen of various areas derived automatically is displayed and correction is received from the operator, for example, even more detailed demands for each individual test can be handled.

(Other Embodiments)

Embodiments are not limited to those described above.

(Acquisition of Three-Dimensional MR Data)

In the embodiments described above, an example in which when three-dimensional MR data is acquired for deriving various areas prior to an imaging scan, 3D FFE is used as a pulse sequence has been explained. However, the embodiment is not limited thereto. When acquiring the three-dimensional MR data, the sequence control unit 120 can use, for example, 3D SSFP or 3D FASE (Fast Asymmetric Spin Echo) as a pulse sequence. For example, in the second embodiment, because the vascular system such as the portal vein, the mesenteric vein, and the splenic vein is used as a landmark, the accuracy of the area derivation can be increased by acquiring the three-dimensional MR data by using the pulse sequence in which the blood in the vascular system is drawn with a high signal value. For example, the sequence control unit 120 can use two or more types of pulse sequences together. In this case, the area deriving unit 133b can derive respective areas from the respective pieces of MR data and use the results thereof together.

For example, the sequence control unit 120 can acquire the three-dimensional MR data by multi-slice imaging using 2D FFE, 2D SSFP, or 2D FASE. For example, the sequence control unit 120 can add a pulse sequence in which a T2 preparation pulse is applied prior to execution of these pulse sequences. By applying the T2 preparation pulse, image contrast can be enhanced.

(Three-dimensional, Two-dimensional)

In the embodiments described above, an example in which the three-dimensional MR data is acquired for the area derivation, and thereafter, the three-dimensional imaging scan is performed has been explained. However, the embodiment is not limited thereto. For example, the sequence control unit 120 can acquire three-dimensional MR data for the area derivation, and thereafter, two-dimensional imaging scan can be performed. For example, the sequence control unit 120 can acquire two-dimensional MR data for the area derivation, and thereafter, the three-dimensional or two-dimensional imaging scan can be performed.

For example, the first embodiment has been explained while assuming a three-dimensional imaging scan in which the whole heart is imaged; however, the embodiment is not limited thereto. For example, the sequence control unit 120 can perform a two-dimensional imaging scan in which a basic cross section of the heart is cine-imaged. The basic cross section refers to a cross section of the heart based on the anatomical characteristic of the heart, and for example, includes a vertical long axis image, a horizontal long axis image, a two chamber long axis image, a three chamber long axis image, a four chamber long axis image, and a left ventricular short axis image. For example, the sequence control unit 120 can calculate a basic position, which is position information for acquiring the basic cross section, from the three-dimensional MR data acquired for the area derivation, and acquire the basic cross section based on the calculated basic position.

(Derivation of Other Areas)

In the embodiments described above, an example in which an application area of a motion detection pulse or an application area of a tag pulse is derived in addition to an imaging scan area from MR data acquired for area derivation has been explained; however, the embodiment is not limited thereto. The area deriving unit 133b can derive an application area of various pulses accompanied with spatial position setting from the MR data acquired for the area derivation. For example, the area deriving unit 133b can derive (one or plural) application areas of a saturation pulse or other ASL pulses.

Furthermore, the area deriving unit 133b can derive not only the application area of various pulses but also other areas from the MR data acquired for the area derivation. For example, the area deriving unit 133b detects an upper end position or a lower end position of a heart from the MR data, to derive an imaging scan range for acquiring a multi-slice image. Further, for example, the area deriving unit 133b can detect a cuboid area circumscribed to the subject P from the MR data to derive a range wider than the cuboid area as the imaging scan range for capturing an image of the sensitivity map. For example, the area deriving unit 133b can detect a cuboid area circumscribed to the heart from the MR data to derive a predetermined range including the cuboid area as an imaging scan range for imaging scan by shimming.

Further, at the time of deriving the imaging scan area, the area deriving unit 133b can derive the number of slices, the slice thickness, and the slice gap to be acquired in the three-dimensional imaging scan area together. For example, when the slice thickness and the slice gap are set in the protocol as fixed values, the area deriving unit 133b calculates the number of slices associated with derivation of the imaging scan area. For example, when the number of slices and the slice gap are set in the protocol as fixed values, the area deriving unit 133b calculates the slice thickness associated with derivation of the imaging scan area. For example, when the slice thickness and the number of slices are set in the protocol as fixed values, the area deriving unit 133b calculates the slice gap associated with derivation of the imaging scan area. For example, if the number of slices is fixed, an imaging scan time can be maintained constant, and if the slice thickness is adjusted, the spatial resolution can be adjusted.

(Image Processing)

Image processing for the area derivation is not limited to the embodiments described above. In the embodiments described above, a registration method for matching the input image with the model image has been explained; however, the embodiment is not limited thereto. For example, a method of deriving respective areas by deforming the model image to register the model image with the input image can be used. Furthermore, for example, the area deriving unit 133b can derive the imaging scan area and the related area by a method not using the model image. For example, the area deriving unit 133b performs threshold processing with respect to the three-dimensional image, thereby segmenting the image into an air area and an area other than the air. Subsequently, the area deriving unit 133b applies a diaphragmatic surface model or a spherical model simulating a heart to the boundary of the air area, thereby detecting the positions of the heart and the top of the convex surface of a diaphragm. The area deriving unit 133b uses these positions as the positions of landmarks to derive the imaging scan area and the application area of the motion detection pulse.

In the embodiments described above, image processing using the model image has been explained; however, a plurality of types of model image can be prepared, for example, according to the age, pre-existing disorder, and the like. In the embodiments described above, the method of selecting the model image based on the input imaging scan conditions has been explained. However, for example, the area deriving unit 133b can select an appropriate model image based on the information of the age, pre-existing disorder, and the like of the subject P input as items for the test.

In the embodiments described above, a method of selecting a model image based on the input imaging scan conditions has been explained; however, the embodiment is not limited thereto. For example, it is assumed here that MR data is acquired for area derivation, and a three-dimensional image generated from the MR data is stored in the storage unit 132 in a data structure based on the DICOM (Digital Imaging and Communications in Medicine) standard. In this case, the area deriving unit 133b can select a model image or the like, for example, based on additional information attached to a three-dimensional image (for example, "heart", "3D FFE", or the like). The additional information is not limited, for example, to the additional information of the DICOM standard, and can be additional information specific to the MRI apparatus 100.

In the embodiments described above, further, an example in which the area deriving unit 133b automatically selects and reads a model image has been explained; however, the embodiment is not limited thereto. For example, the area deriving unit 133b can display a list of the model images prepared in plural numbers and receive selection of a model image from an operator. In this case, the area deriving unit 133b uses the model image selected by the operator for derivation of various areas. For example, the area deriving unit 133b can narrow down model images as list display targets from the plurality of model images based on information of, for example, the imaging scan conditions, the age of the subject P, the pre-existing disorder, and the like, so as to list-display only the narrowed-down model images.

The MRI apparatus 100 according to the embodiments described above can realize reselection of the model image and rederivation of various areas based on the re-selected model image, at a stage of the preparation scan or at a post stage of the imaging scan. For example, in the embodiments described above, an example in which the area deriving unit 133b displays the confirmation screen and receives a correction input on the confirmation screen has been explained (Steps S107 to S109 in FIG. 4). However, the area deriving unit 133b can perform reselection of the model image and rederivation of various areas based on the re-selected model image at this stage. For example, the area deriving unit 133b displays a "model image reselection" button together with the confirmation screen. When this button is pressed, the area deriving unit 133b automatically selects a new model image or displays a list of model images, to receive selection of a new model image from an operator. Thereafter, the area deriving unit 133b uses the new model image newly selected to rederive various areas.

For example, in the embodiments described above, an example in which the image generating unit 136 displays images acquired and generated by the imaging scan on the display unit 135 has been explained (Steps S112 to S113 in FIG. 4). However, the area deriving unit 133b can perform reselection of the model image and rederivation of various areas based on the re-selected model image at this stage. For example, the area deriving unit 133b displays a "model image reselection" button together with the images acquired by the imaging scan. When this button is pressed, the area deriving unit 133b automatically selects a new model image or displays a list of model images, to receive selection of a new model image from the operator. Thereafter, the area deriving unit 133b uses the new model image newly selected to rederive various areas. In this case, the imaging scan is also performed again.

(Specific Numerals, Processing Orders)

In principle, specific numerals and processing orders exemplified in the embodiments described above are only examples. For example, the landmarks used for derivation of various areas can be changed arbitrarily. Furthermore, the processing orders can be changed arbitrarily as well, for example, a process procedure in which a confirmation screen is not displayed. Further, specific pulse sequences can be changed arbitrarily.

(Image Processing System)

In the embodiments described above, an example in which the MRI apparatus 100, which is a medical diagnostic imaging apparatus, performs various processes has been explained; however, the embodiment is not limited thereto. For example, an image processing system including the MRI apparatus 100 and an image processing apparatus can perform the various processes described above. The image processing apparatus is, for example, a workstation, an image storage apparatus (an image server) and a viewer in a PACS (Picture Archiving and Communication System), and various apparatus in an electronic health record system. In this case, for example, the MRI apparatus 100 performs acquisition by the sequence control unit 120. Meanwhile, the image processing apparatus receives the MR data and space-k data acquired by the MRI apparatus 100 from the MRI apparatus 100 or from the image server via a network, or receives the MR data and space-k data input by an operator via a recording medium, and stores these pieces of data in the storage unit. Thereafter, the image processing apparatus can perform the various processes described above (for example, the process performed by the image generating unit 136 and the process performed by the area deriving unit 133b) with respect to the MR data and space-k data stored in the storage unit.

(Program)

Instructions shown in the process procedure in the embodiments described above can be performed based on a program which is software. It is possible to configure such that a general-purpose computer stores therein the program in advance and then reads the program so as to achieve effects identical to those of the MRI apparatus 100 of the embodiment described above. The instructions described in the embodiments described above are recorded in a magnetic disk (a flexible disk, a hard disk, and the like), an optical disk (a CD-ROM, a CD-R, a CD-RW, a DVD-ROM, a DVD±R, a DVD±RW, and the like), a semiconductor memory, or a recording medium similar to those, as a program that can be executed by a computer. As long as the computer or embedded system is a readable storage medium, the storage format thereof can be of any type. As the computer reads the program from the recording medium and executes the instructions described in the program on a CPU based on the program, it is possible to realize operations identical to those of the MRI apparatus 100 according to the embodiments described above. Furthermore, the computer can acquire or read the program through a network when the computer acquires or reads the program.

An OS (Operating system) operated on a computer based on the instructions of a program installed in the computer or an embedded system from a storage medium, MW (Middleware) such as database management software and a network, and the like can perform a part of respective processes for realizing the embodiments described above. Furthermore, the storage medium is not limited to a medium independent of the computer or the embedded system, and includes the storage medium stored or temporarily stored by downloading a program transmitted through a LAN (local Area Network), the Internet, and the like. Further, the storage medium is not limited to one medium, and a case where the processes in the embodiments described above are performed by a plurality of mediums can be also included in the example of using a storage medium in the above embodiment, and configurations of the media can be of any type.

The computer or the embedded system in the embodiments is to perform respective processes in the embodiments described above and can be of any configuration such a apparatus configured of any one of a personal computer, a microcomputer and the like, or a system in which a plurality of apparatus are connected by a network. The computer in the embodiments is not limited to a personal computer, but can be an arithmetic processing unit incorporated in an information processor, a microcomputer, and the like, and the computer collectively represents an apparatus or a apparatus that can realize functions in the embodiments by a program.

According to the magnetic resonance imaging apparatus and the magnetic resonance imaging method of at least one of the embodiments described above, various areas can be easily set.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging (MRI) apparatus comprising:
   MRI system components including static and gradient magnetic field generators, at least one radio frequency (RF) coil, RF transmitter and receiver circuits and at least one controlling processor configured to:
   execute (i) a first imaging scan acquiring data in a range including a target internal organ and (ii) a second imaging scan acquiring data for a diagnostic image by controlling execution of pulse sequences;
   generate an image by using data acquired by the first imaging scan; and
   derive (i) an imaging scan area, by image processing using the first scan image and a model image, in which data for the diagnostic image are to be acquired in the second imaging scan and (ii) a related area set associated with the imaging scan area in the second imaging scan.

2. The apparatus according to claim 1, wherein the at least one processor is configured to detect both a landmark used for deriving the imaging scan area and a landmark used for deriving the related area from the first scan image, and to derive the imaging scan area and the related area based on the detected landmarks.

3. The apparatus according to claim 1, wherein the at least one processor is configured to derive the imaging scan area and the related area after adjusting a mutual positional relation between the imaging scan area and the related area.

4. The apparatus according to claim 1, wherein said at least one processor is further configured to receive an imaging scan condition setting that includes an input of imaging scan conditions, wherein
   the model image to be used for the image processing is selected based on the imaging scan conditions, for which an input has been received.

5. The apparatus according to claim 1, wherein the at least one processor is configured to
   execute the first imaging scan acquiring data of a range including a heart and a diaphragm and the second imaging scan acquiring data of the whole heart for a diagnostic image,
   use data acquired by the first imaging scan to generate an image including the heart and the diaphragm, and
   detect positions of the heart and an apex of a convex surface of the diaphragm from the image based on image processing and derive a heart area and an application area of a motion detection pulse for detecting a respiratory motion to move the imaging scan area, based on the detected positions.

6. The apparatus according to claim 5, wherein the heart area and the application area of the motion detection pulse are derived after adjusting a mutual positional relation thereof so that the heart area and the application area of the motion detection pulse do not overlap on each other.

7. The apparatus according to claim 1, wherein the first imaging scan acquires data of a range including a liver and a portal vein and second imaging scan acquires data of the portal vein for a diagnostic image by using a Time-SLIP (Spatial Labeling Inversion Pulse),
   data acquired by the first imaging scan is used to generate an image including the liver and the portal vein, and
   positions of the liver and a bifurcation between the portal vein and mesenteric veins are detected from the image based on image processing, and the imaging scan area and an application area of a tag pulse are derived.

8. The apparatus according to claim 1, wherein at least one of a position, a size, and a direction for the imaging scan area and the related area are derived.

9. The apparatus according to claim 1, wherein the first imaging scan and the second imaging scan are repeatedly executed alternately.

10. The apparatus according to claim 1, wherein a list of model images to be used for the image processing is displayed and selection of a model image is received from an operator.

11. A magnetic resonance imaging method executed by a magnetic resonance imaging apparatus, comprising:
 executing a first imaging scan acquiring data of a range including a target internal organ and a second imaging scan acquiring data for a diagnostic image by controlling execution of a pulse sequence;
 generating an image by using data acquired by the first imaging scan; and
 deriving an imaging scan area in which the data for the diagnostic image are acquired in the second imaging scan and a related area set associated with the imaging scan area in the second imaging scan, based on image processing using the image and a model image.

12. The method according to claim 11, further comprising:
 displaying a GUI (Graphical User Interface) for receiving an input of imaging scan conditions;
 generating sequence information according to the received imaging scan conditions on the GUI, the first imaging scan being executed by executing a pulse sequence based on the generated sequence information,
 wherein the deriving displays a confirmation screen for the operator to confirm the derived imaging scan area and the derived related area, receives a confirmation input or a correction input at least one of the derived imaging scan area and the derived related area on the confirmation screen, and displays, when the correction input has been received, the confirmation screen again for the operator to confirm the corrected area.

13. The method according to claim 12, wherein the executing, when the confirmation input has been received, sets the imaging scan area and the related area each of which is confirmed on the confirmation screen, and executes an imaging scan including the first imaging scan and the second imaging scan.

14. The method according to claim 12, wherein the executing, when the confirmation input has been received, performs preparation scans including at least a scan for acquiring profile data indicating a sensitivity of each coil element or each channel in an array direction, a scan for acquiring sensitivity maps indicating a sensitivity distribution of each coil element or each channel, a scan acquiring spectrum data for obtaining a center frequency of an RF pulse, and a scan for obtaining a current value that is caused to flow in a correction coil in order to adjust uniformity of a magnetostatic field, sets the imaging scan area and the related area, each of which is confirmed on the confirmation screen, and executes an imaging scan including the first imaging scan and the second imaging scan.

15. The method according to claim 12, wherein
 the displaying displays a model diagram of human body for receiving a selection of an image-captured region on a first GUI, and further displays, when a selection of the image-captured region has been received on the first GUI, a list of generic terms of a group of pulse sequences relating to the selected image-captured region on a second GUI.

16. The method according to claim 15, wherein
 the displaying further displays, when a selection of a generic term for imaging the selected image-captured region has been received on the second GUI, a list of a group of pulse sequences corresponding to the selected generic term on a third GUI, and
 the generating the sequence information generates, when a specification of a group of pulse sequences to be executed has been received on the third GUI, the sequence information according to the specified group of pulse sequences.

17. The method according to claim 12, wherein the deriving
 reads the model image in which positions of a heart and a top of a convex surface of a diaphragm are known when the imaging scan conditions is corresponding to an imaging scan of the heart,
 performs rigid deformation or non-rigid deformation as the image processing with respect to the image so that the image is matched with the model image,
 identifies positions of the heart and the top of the convex surface of the diaphragm in the deformed image,
 performs inversely deformation of the deformed image,
 detects positions of the heart and the top of the convex surface of the diaphragm in the inversely deformed image, and
 derives the imaging scan area including the heart and the related area which is an application area of a motion detection pulse for detecting a respiratory motion to move the imaging scan area, based on the detected positions.

18. The method according to claim 12, wherein the deriving
 reads the model image in which positions of a liver, a spleen, a portal vein and mesenteric veins when the imaging scan conditions is corresponding to an imaging scan of the portal vein,
 performs rigid deformation or non-rigid deformation as the image processing with respect to the image so that the image is matched with the model image,
 identifies positions of the liver, the spleen, the portal vein and the mesenteric veins in the deformed image,
 performs inversely deformation of the deformed image,
 detects positions of the liver, the spleen, the portal vein and the mesenteric veins in the inversely deformed image, and
 derives the imaging scan area including the liver and the spleen and the related area which is an application area of a tag pulse.

19. The method according to claim 12, wherein the deriving detects a heart as a landmark used for deriving the imaging scan area and a diaphragm as a landmark used for deriving the related area from the image, and derives the imaging scan area including the heart and the related area which is an application area of a motion detection pulse for detecting a respiratory motion to move the imaging scan area, based on the detected landmarks.

20. A magnetic resonance imaging system comprising:
 a processor; and
 a memory that stores processor-executable instructions that, when executed by the processor, cause the processor to:
 execute a first imaging scan acquiring data in a range including a target internal organ and a second imaging scan acquiring data for a diagnostic image by controlling execution of a pulse sequence;
 generate an image using data acquired by the first imaging scan; and
 derive an imaging scan area in which data for the diagnostic image are acquired in the second imaging scan and a related area set associated with the imaging scan area in the second imaging scan, based on image processing using the image.

21. The apparatus according to claim 1, wherein the model image includes a model of the target internal organ.

22. The apparatus according to claim 1, wherein the imaging processing includes rigid deformation or non-rigid deformation.

* * * * *